（12) United States Patent
Fuisz et al.

(10) Patent No.: US 6,337,082 B1
(45) Date of Patent: Jan. 8, 2002

(54) SACCHARIDE-BASED MATRIX

(76) Inventors: Richard C. Fuisz, 1287 Ballantree Farm Dr., McLean, VA (US) 22101; Robert K. Yang, 138-10 Franklin Ave. No. 2-C, Flushing, NY (US) 11355

( * ) Notice: Subject to any disclaimer, the term of this patent is extended or adjusted under 35 U.S.C. 154(b) by 0 days.

(21) Appl. No.: 09/003,996

(22) Filed: Jan. 7, 1998

Related U.S. Application Data

(63) Continuation-in-part of application No. 08/482,778, filed on Jun. 7, 1995, now Pat. No. 5,709,876, which is a division of application No. 08/365,591, filed on Dec. 28, 1994, now Pat. No. 5,597,608, which is a division of application No. 07/847,595, filed on Mar. 5, 1992, now Pat. No. 5,387,431, which is a continuation-in-part of application No. 07/782,430, filed on Oct. 25, 1991, now abandoned.

(51) Int. Cl.⁷ .................................................. A61K 9/26
(52) U.S. Cl. ........................ 424/439; 424/484; 424/493; 424/488; 424/418; 424/410
(58) Field of Search ................................. 424/439, 484, 424/410, 493, 418, 488

(56) References Cited

U.S. PATENT DOCUMENTS

| 5,096,492 | A | | 3/1992 | Fuisz | 106/215 |
|---|---|---|---|---|---|
| 5,286,513 | A | | 2/1994 | Fuisz | 426/641 |
| 5,374,447 | A | | 12/1994 | Fuisz | 426/641 |
| 5,387,431 | A | | 2/1995 | Fuisz | 426/658 |
| 5,429,836 | A | | 7/1995 | Fuisz | 426/601 |
| 5,431,950 | A | | 7/1995 | Fuisz | 426/641 |
| 5,490,993 | A | | 2/1996 | Fuisz | 426/92 |
| 5,597,608 | A | * | 1/1997 | Fuisz | 426/658 |
| 5,709,876 | A | | 1/1998 | Fuisz | 424/439 |

* cited by examiner

Primary Examiner—Thurman K. Page
Assistant Examiner—William E. Benston, Jr.
(74) Attorney, Agent, or Firm—John F. Levis; Richard D. Schmidt

(57) ABSTRACT

The present invention is a saccharide-bsed matrix and the product resulting therefrom made from a maltodextrin feedstock subjected to conditions which induce flash flow of the maltodextrin so that the matrix possesses a physically- or chemically-altered structure from the feedstock. The present invention also includes a method of producing the matrix and of making products which take advantage of the unique properties of the matrix. Such products include, but are not limited to, unique colloidal-like dispersions and suspensions made from the matrix.

24 Claims, No Drawings

US 6,337,082 B1

SACCHARIDE-BASED MATRIX

The present application is a continuation-in-part of U.S. patent application Ser. No. 08/482,778 filed Jun. 7, 1995, now U.S. Pat. No. 5,709,876 which is a division of U.S. patent application Ser. No. 08/365,591 filed Dec. 28, 1994 (and issued as U.S. Pat. No. 5,597,608), which is a division of U.S. patent application Ser. No. 07/847,595 filed Mar. 5, 1992 (and issued as U.S. Pat. No. 5,387,431), which is a continuation-in-part of U.S. patent application Ser. No. 07/782,430 filed Oct. 25, 1991, now abandoned, Mar. 9, 1994.

BACKGROUND OF THE INVENTION

The present invention relates to a new saccharide-based matrix which can be used in food products and to a method of making same, as well as methods of using the new material.

Food technology in recent years has focused on providing high quality food products which are low in calorie content and low in cost. Similarly, the pharmaceutical industry is concerned with efficient delivery systems which are relatively inexpensive and accessible. To this end, ingredients are constantly being sought for their versatility and compatibility with major food products and common medicaments such as analgesics, antibiotics, etc.

Carbohydrates have always been a major component of the human diet. Sugars, in particular, have been used extensively as a food ingredient. Materials containing both simple sugars and polymers of saccharides have also been used as ingredients in food products in pharmaceutical delivery systems. Food grade saccharides are available as mon-, di-, tri-, tetra-, pentasaccharides and oligomers and as carbohydrates having a large number of monosaccharide molecules, e.g., greater than 10 monosaccharide units, which are known as polysaccharides.

Saccharide-based products can have varying degrees of low-monomer saccharides, or sugars, oligomers, and polysaccharides, such as starch. Some saccharide-based products are prepared by hydrolysis of starch and are classified by the degree of starch polymer hydrolysis. The measuring unit is referred to as D.E. or dextrose equivalent. D.E. is defined as reducing sugars expressed as dextrose and reported as a percentage of the dry substance.

A saccharide-based product having high short-carbon-chain content, e.g, glucose and low-unit oligomers thereof, usually results in a higher dextrose equivalent (D.E.). However, saccharide-based material having greater long-carbon-chain content, e.g, high monomer unit oligomers and polymers, usually results in a lower D.E. rating.

For example, maltodextrins contain a mix of sugars and polysaccharides which range from long-chain oligomers resulting from starch hydrolysis to sugars having a low number of monomeric units. Under FDA guidelines, maltodextrin consists of non-sweet, nutritive saccharide polymers having a D.E. of less than 20, while corn syrup solids is regarded by the FDA as having a D.E. greater than 20. The present inventors, however, refers to maltodextrins collectively as saccharide-based material consisting of non-sweet nutritive saccharide polymers and other oligomers having six-carbon monomer units which collectively provide a carrier material capable of forming a matrix.

Maltodextrins have been used as a nonfat additive. One of the greatest advantages of maltodextrins is that they do not act adversely on the intestinal tract. Consequently, they are particularly useful as a bulking agent as a fat substitute. Moreover, maltodextrins are generally recognized as safe (GRAS) by the united States Food and Drug Administration.

Unfortunately, the ability to disperse maltodextrins and to use them in different products is limited by their physical and chemical cohesiveness. They are unlike their high sugar counterparts in that they are relatively unreactive and physically resistive to mixing and dispersing. While artisans have been able to process sugar to enhance its utility in food and medicaments, the maltodextrins do not appear to be as versatile.

In U.S. Pat. No. 4,855,326, issued Aug. 8, 1989, various substances having pharmacological properties were combined with sugar and spun into fibers to product a water-soluble product. The various examples enumerated in the patent all involved the use of water-soluble medicaments and were directed to enhancing the solubility rate of the different substances. The patent describes methods for combining a medicament with any one or more of the water soluble melt spinnable sugars and spinning the combination to produce a readily soluble floss form of the medicament. The disclosure of such patent is incorporated herein by reference.

In U.S. Pat. No. 5,011,532, issued Apr. 30, 1991, oleaginous substances such as vegetable oil, mineral oil, baby oil, margarine, lanolin, cocoa butter and the like are disclosed as characteristically lacking affinity for water. The '532 patent explains how this characteristic is altered by mixing the oleaginous substance with sugar and melt-spinning the mixture in a cotton candy spinning machine or the equivalent. As so modified, the products disperse in water, forming a colloidal or pseudo-colloidal dispersion. Such modification enabled such widely disparate procedures as (1) incorporating shortening oil in a cake mix containing flour but no egg to which water is added to produce a batter, and (b) producing a confection or medicated lozenge by dehydrating the dispersion and allowing the melted residue to solidify. The disclosure of the '532 patent is incorporated herein by reference.

Other disclosures dealing with spinning substances with one or more sugars will be found in U.S. Pat. Nos. 4,873,085, 4,997,856, 5,028,632, and 5,034,421, issued, respectively, Oct. 10, 1989, Mar. 5, 1991, Jul. 2, 1991, and Jul. 23, 1991.

The above-identified disclosures are directed to melt-spinning sugar by introducing the sugar to a cotton candy spinning machine. Generally such equipment is operated at a room temperature of around 200° C. at a speed of about 3500 r.p.m. Melt-spin in such equipment relies on the characteristics of sucrose, such as high crystallinity and high physical and chemical lability. Thus, it has been the belief of the artisan that sucrose is an important ingredient in feedstock for melt-spin processing.

In fact, attempts to spin low-sucrose-containing saccharides have been generally unsuccessful. Feedstock having low D.E. or no sucrose as a carrier component chars during melt-spinning and is generally non-processible, especially on a commercial scale.

SUMMARY OF THE INVENTION

The present invention includes a saccharide-based matrix resulting from a maltodextrin feedstock which has been subjected to melt-spin conditions sufficient to induce flash flow of the feedstock so that the resulting matrix possesses physically- or chemically-altered structure from that of the feedstock. The maltodextrin feedstock of the present invention is a saccharide-based solid material consisting of non-sweet, nutritive saccharide polymers and other glucose-bearing oligomers as well as glucose units, which collectively provide a carrier material capable of forming a matrix. The dextrose equivalent (D.E.) of the maltodextrin feedstock is less than 40, and in a preferred embodiment is between 20 and 40. In yet another preferred embodiment, the maltodextrin has a D.E. between 10 and 20.

Maltodextrins useful herein are solid maltodextrins. Examples of solid maltodextrins are those which have a D.E. of up to about 45 D.E. Several useful maltodextrins have a D.E. of 42. It is intended to include these maltodextrins within the scope of the present invention.

The carrier component provided by the feedstock has a high glucose profile. A high glucose profile means that the elements include a large amount of six-carbon mono- and disaccharides as well as other glucose-based oligomers.

Preferably the combined amount of mono-, di-, and tri-saccharides in the feedstock is 25% or greater on a dry solids basis. In other embodiments, the combined amount of mono- and di-saccharides in the feedstock is 15% or greater on a dry solids basis. The feedstock contains no sucrose, or sucrose in insignificant amounts with respect to the overall carbohydrate profile. Is it note that while other materials such as sucrose and other sugars may be incorporated in the feedstock for other purposes, the resulting method and product will still be within the present invention.

The process of the present invention includes subjecting the feedstock simultaneously to flash heating and applied physical force such that the solid material experiences sufficient internal flow to transform the feedstock to a solid matrix which has a physically- and/or chemically-altered structure from that of the feedstock. The flash heating temperature and the duration of heating, however, is below that which would cause degradation of the maltodextrin feedstock.

In the case of melt-spinning, it has been found that in one embodiment of the invention a flash heat temperature in the range of 140° C. is useful in conjunction with the centrifugal force generated by spinning a head of 5.5 inches in diameter at 3500 r.p.m. The maltodextrin feedstock in the case had a dextrose equivalent of between 34 and 38 and a combination of glucose di- and monosaccharides of about 34 to 35 percent by weight. The carbohydrate profile of the feedstock also includes oligomers having pentasaccharide, i.e., five unit, and greater monomeric unit at level of about 40%. In many embodiments, a flash heat period of less than about five seconds has been found to be effective.

In one separate embodiment, feedstock is primarily maltooligosaccharides. Maltooligosaccharides are produced by selective hydrolysis of corn starch followed by removal of high and low molecular weight compounds. The maltooligosaccharide mixtures includes oligomers having the structure, where n=1 to 8, with trace amounts of higher n. The $G_1$–$G_3$ (i.e., mono-, di- and trimer) content o the feedstock should be at least 25% or greater on a dry solids basis. The maltooligo-saccharide embodiment is particularly suitable for a high energy food product which includes peanut butter in the feedstock or in the end product or in both matrix and end product. Moreover, the resulting maltooligosaccharide mixture, which is usually in the form of a flake, is ideally suited for inclusion of the medicament, or, alternatively, for inclusion of a flavor ingredient.

In certain preferred embodiments, nut paste, such as paste resulting from crushing peanuts, cashews, macadamia nuts, et al., can be included in the feedstock to provide a high-flavor-intensity matrix. The resulting matrix can be used directly in food products or can be reconstituted by addition of a suitable liquid such as water to form a nut cream or butter. In another preferred embodiment, low fat milk, e.g., 2% milk, skim milk, etc., is used as the liquid to achieve viscosity stability even after a period of time. An advantage of processing the nut paste in accordance with the present invention is to provide a reduced-fat and reduced-calorie nut ingredient or product which retains high nut flavor.

A specific embodiment found to be particularly effective as a food ingredient includes a combination of hazelnut paste processed with maltodextrin to produce a flake which can be used as, among other things, a spread, a soft-serve ice cream additive, or a candy center.

Due to rapid dispersibility of nut flakes produced according to the present invention, they can be used as an ingredient for making soft-serve ice cream. The nut flakes can be added directly to a dry mix to which water is subsequently added to produce soft-serve ice cream. Alternatively, nut flakes can be added directly to a liquid mix prior to use in a soft-serve (freezer) machine.

In a further embodiment of the present invention, a saccharide-based matrix incorporating maltodextrin, a gelling agent, and a sugar is provided. The matrix is useful as a gelling composition which is instantaneously dispersible in aqueous medium.

As a result of the present invention, an excellent food grade saccharide-based matrix can be provided for use in foods and in pharmaceuticals. Thus, an essentially non-sweet, low-calorie, inexpensive material can be used as an ingredient for bulking and dispersing in food products. Additional products such as pharmaceuticals, cosmetics and those containing most material suitable for incorporation of the new matrix are contemplated for use in the present invention.

For example, it has also been found that the present invention is quite effective for providing a medicament containing composition which is essentially a suspension of matrix material with a medicament dispersed throughout. This can be achieved in one preferred embodiment by a combination of a matrix prepared by processing a feedstock of maltodextrin and gum by subjection to conditions of flash flow and thereafter mixing it with a medicament to form a mixture or a coating of the medicament on the matrix. The consumer can then add a liquid, such as water, to form a suspension. Alternatively, the medicament can be added during mixing with the water so that a substantially consistent mixture of the medicament is present throughout the suspension. In one preferred embodiment the medicament is sucralfate. Those skilled in the art, however, will appreciate that other medicaments can be used to form the suspension.

A specific embodiment of the present invention which relates to medicines concerns contrast mediums for x-ray technology. In this embodiment, a contrast agent such as barium sulfate ($BaSo_4$) can be spun with maltodextrin and gum to produce a matrix in the form of, for example, a flake. The matrix can then be dispersed in water and ingested for x-ray analysis. This aqueous contrast medium provides excellent adherence to the esophagus and stomach wall and excellent dispersion of the contrast agent throughout the medium.

This new matrix can be used alone or in combination with other ingredients as a means for dispersing the added ingredient throughout the material. For example, the particles, chips, flakes, spicules or combinations thereof can be used to disperse oleaginous materials which are otherwise relatively non-dispersable because of the physical characteristics of such materials. In fact, an oleaginous-containing matrix is useful for retaining oleaginous material with or without emulsifiers in baked goods without the need of a surfactant or other additives for holding such material in dough during preparation.

The applications for this new material are vast. Consequently, food and pharmaceutical artisans have been equipped with a new tool which can be used to significantly enhance food products and medical delivery and industrial systems without unwanted flavor or side effects.

Moreover, the present invention can be used with dyes to provide a saccharide-based matrix with a dye incorporated therein.

For a better understanding of the present invention, reference is made to the following description and its scope will be pointed out in the appended claims.

DETAILED DESCRIPTION OF THE INVENTION

The present invention concerns the formation of a new solid matrix material from a maltodextrin feedstock. Maltodextrins are composed of water-soluble glucose polymers obtained from the reaction of starch with acid or enzymes in the presence of water. The hydrolysis reaction produces a carbohydrate mixture of saccharides having a dextrose equivalent (D.E.) of less than 20, or greater than 20 when the hydrolysis proceeds to produce what the FDA has termed corn syrup solids.

The maltodextrin of the present invention, however, has been selected as possessing unique properties for purposes of the present invention. Specifically, the maltodextrin feedstock of the present invention includes a carrier component which is capable of being processed from a solid through a flash flow condition to a new solid having altered physical and chemical structure. Moreover, the maltodextrins of the present invention are those mixtures resulting from hydrolysis as described above which have a D.E. of less than 40. In a preferred embodiment of the present invention, the D.E. is between 2 and 40, and in yet another preferred embodiment the D.E. is between 10 and 20. As previously explained, the present invention contemplates processing of solid maltodextrins, e.g., those having a D.E. of up to about 45. These higher D.E. solid maltodextrins are within the scope of the present invention. Maltodextrins which are useful in the present invention include some products which are sold under the trademark MALTRIN®, a product of the Grain Processing Corporation of Muscatine, Iowa.

More recently, it has been discovered that a deionized form of maltodextrin is especially useful. Deionization, in general, refers to the procedure whereby ionic impurities are removed by, for example, passing the material to be deionized through cation and/or anion exchange columns. In the present preferred embodiment, deionized maltodextrin ENZOSE 42DE, a product of CPC International, has been found to be particularly beneficial in processing according to the present invention.

The inventive matrix of the present invention is prepared by subjecting solids as described above to a melt-spin process (or conditions comparable thereto) which provide sufficient internal flow to permit the transition in structure without degradation of the material. Internal flow occurs when the infrastructure of the material breaks down sufficiently to permit movement of material at a subparticle level, and probably at a molecular level. At a molecular level, internal flow contemplates the movement of molecules relative to each other.

The delivery systems of the present invention have a substantially amorphous flash-flow-formed matrix. The term "flash-flow" refers to a process of subjecting the feedstock, e.g., matrix material and, optionally, hydrophobic oil, simultaneously to flash heating and applied physical force such that the solid matrix material experiences sufficient internal flow to transform it to a physically and/or chemically-altered structure from that of the feedstock.

Flash-flow processing can be accomplished in several ways. Flash heat and flash shear are two such processed which can be used. In the flash heat process, the feedstock material is heated sufficiently to create an internal flow condition which permits part of the feedstock to move at a subparticle level with respect to the rest of the mass and exit openings provided in the perimeter of, for example, a spinning head. The centrifugal force created in the spinning head flings the flowing feedstock material outwardly from the head so that it reforms with a changed structure. The force required to separate and discharge flowable feedstock is only the centrifugal force created by the spinning head. The flash heat process is one process for producing the amorphous matrix resulting from this invention.

In the flash shear process, a shearform matrix is formed by raising the temperature of the feedstock material which includes a non-solubilized carrier to a point where the carrier material undergoes internal flow upon application of a fluid shear force. The feedstock is advanced and ejected while in internal flow condition, and subjected to disruptive fluid shear forces to form multiple parts or masses which have morphology different from that of the original feedstock.

The multiple masses are cooled substantially immediately after contact with the fluid shear force and are permitted to continue in a free-flow condition until solidified.

The feedstock material includes maltodextrin as defined herein and, optionally, other material such as an oleaginous substance.

The flash shear process can be carried out in an apparatus which has means for increasing the temperature of a non-solubilized feedstock and means for simultaneously advancing it for ejection. A multiple heating zone twin screw extruder can be used for increasing the temperature and advancing feedstock. The second element of the apparatus is a means for ejecting the feedstock in a condition for shearing it to provide the shearform matrix. The means for ejecting is in fluid communication with the means for increasing the temperature and is arranged at the point to receive the feedstock while it is in the internal flow conditions. The means for ejecting the feedstock is preferably a nozzle which provides high pressure ejection of the feedstock material. For a description of various apparatus which can be used to produce the inventive delivery systems, see, for example, U.S. Pat. No. 5,380,473 dated Jan. 10, 1995, entitled *PROCESS FOR MAKING SHEARFORM MATRIX*, and U.S. Pat. No. 5,427,811 dated Jun. 27, 1995, entitled *METHOD AND APPARATUS FOR SPINNING THERMO-FLOW MATERIALS*, which are incorporated herein by reference.

One preferred flash-flow process used to form the inventive matrix involves spinning a feedstock in a "cotton candy" fabricating type machine such as that described in pending U.S. patent application Ser. No. 08/854,344 filed May 12, 1997. The spinning machine used to achieve a flash heat process may also be a cotton candy type machine such as the Econo-Floss Model 3017 manufactured by Gold Metal Products Company of Cincinnati, Ohio. It will be appreciated by those skilled in the art that any apparatus or physical process which provides similar forces and temperature gradient conditions can also be used. For simplicity in disclosing and describing this invention, the terms "flash heat" will be understood to mean a process which includes subjecting a feedstock to the combination of temperature, thermal gradients, flow, flow rates, and mechanical forces of the type produced in a cotton candy machine. The apparatus is operated at the temperature and speed which permit flash-flow of the feedstock without significant deterioration of ingredients. The resulting matrix may be in the form of a floss, fiber, particle, flake, spicule or any other generally nondescript amorphous aggregate.

Internal flow of material is generally associated with melting point or glass transition point. However, it is contemplated that the combined application of heat and external force is sufficient to produce the flow at temperatures below the melting or glass transition point for most compositions.

It is only when the unique combination of selected feedstock and appropriate conditions are applied thereto that the unique matrix material can be produced in accordance with the present invention. Elements outside these conditions appear to prevent or retard processability.

In fact, various experiments carried out using saccharide-based materials of varying composition demonstrated that processing maltodextrins indiscriminately with melt-spinning apparatus resulted in charring of the feedstock and non-processability of the material. The non-processability resulted in the material being only partially spun, and other deteriorative effects on the resulting matrix. In fact, when maltodextrins were combined with varying amounts of corn oil and polydextrose, the resulting product was charred and the spinning heat of the apparatus became clogged. For example, when a 23-gram sample of dried soup was mixed with 12 grams of maltodextrin and 12 grams of corn oil, the mixture would not spin through the spinning apparatus.

In further experiments, maltodextrins were intimately contacted with corn oil by processing in a food processor. When the blended material was melt-spun, the resulting material was charred and brown in color. The mixture was then added to water, but much of it did not readily dissolve. Furthermore, it had a burned flavor and was generally quite unacceptable for any use whatsoever. Even when lower temperatures were used in the spinning apparatus, the mixture of maltodextrins and corn oil resulted in brown woodchip-appearing material with a display of fringe floss-like material. The substance dispersed in water, but appeared to be very oil and did not demonstrate any noticeable miscibility.

Other experiments tried using maltodextrin in combination with corn oil and additives such as salt resulted, once again, in charring and unsatisfactory matrix product.

Surprisingly, however, it has been found that if the feedstock is correctly tuned and subjected to correct melt-spinning conditions, a completely new matrix material can be produced which results from the alteration of the physical and/or chemical structure of the original feedstock. This fine-tuning of the ingredients and process parameters includes the use of a maltodextrin feedstock as defined herein which has a matrix capable of undergoing the specified transition. This feedstock is introduced to the apparatus as a solid material and the resulting matrix is also a solid material.

The apparatus is operated at a temperature and speed which permits flash flow, but does not deteriorate the material undergoing thee process. Consequently, there is no resulting charring or clogging, nor is there unwanted side product having a different characteristic than that which is desired. Usually, the resulting matrix is in the form of a particle, flake, spicule, or other generally nondescript aggregate capable of subsequent processing in accordance with generally accepted techniques.

Furthermore, the feedstock material usable in the present invention is capable of being processed with additional component(s) which are incorporated in the desired product but do not distract from its appearance or utility. Thus, the maltodextrin solids and the additive contained in the solids can be altered with respect to various characteristics, including dispersability and mixability, in, or with, various media. In some aspects, the products of the present invention can be used in lieu of freeze-dried materials.

The nature and amount of other component or components used with the maltodextrins will vary the properties of the mixture from the standpoint of spinning. The addition of water or other liquids changes the rheology of the melt-spun material and can have an effect on the size and shape of the flakes and/or spicule-like particles.

Thus, the matrix can be used to carry oleaginous substances and permit the use of such oleaginous materials to be dispersed easily and uniformly in other materials such as foods. The oleaginous materials can be included in the melt-spun maltodextrin feedstock with numerous hydrophobic materials with which oleaginous materials would otherwise be incompatible. Moreover, a variety of hydrophobic materials can be combined in a product such as food or otherwise, and yet be able to perform their separate functions when and if they are exposed to an aqueous media.

Thus, in one aspect of the invention, ingestible food and food ingredient materials can be admixed and combined with the maltodextrin prior to melt-spinning of the mixture. Ingredients suitable for admixture with the maltodextrin starting material include ready-to-use products such as soup mixes, beverage mixes, food sauces, gravy mixes, condiments, flavor compositions and components of flavor compositions, nutritional supplements, low-calorie food materials, food conditioning agents, dehydrated vegetable fluids such as orange juice and tomato juice, dehydrated animal fluids such as beef "extract," oils, fats, natural and/or synthetic sweeteners, acidifying agents, alkalizing agents, food supplements such as vitamins and/or minerals, extracts, spices, seasonings, aminio acids, polypeptides, reducing sugars to permit Maillard browning, and food grade vehicles such as propylene glycol and the like.

Another of the important uses for the solids and corn syrup solid-based materials provided by the processes of this invention is the preparation of pharmaceutical materials.

Suitable categories of active ingredient which may be employed in the present invention may vary widely. Illustrative categories and specific examples include:

(a) Antitussives such as dextromethorphan, dextromethorphan hydrobromide, noscapine, and chlophedianol hydrochloride;

(b) Antihistamines such as chlorpheniramine maleate, phenindamine tartrate, doxylamine succinate, and phenyltoloxamine citrate;

(c) Decongestants such as phenylephrine hydrochloride, phenylpropanolamina hydrochloride, pseudoephedrine, hydrochloride ephedrine;

(d) Various alkaloids such as codeine phosphate, codeine sulfate and morphine;

(e) Mineral supplements such as potassium chloride and calcium carbonates, magnesium oxide and other alkali metal and alkaline earth metal salts;

(f) Laxatives, vitamins and antacids;
(g) Ion exchange resins such as cholestyramine;
(h) Anti-cholesterolemic and anti-lipid agents;
(i) Antiarrhythmics such as N-acetyl-procainamide;
(j) Antipyretics and analgesics such as acetaminophen, aspirin and ibuprofen;
(k) Appetite suppressants such as phenylpropanolamine hydrochloride or caffeine;
(l) Expectorants such as guaifenesin; and
(m) hormones, antibodies, antigens, and other bio-agents.

A non-limiting list of other active ingredients includes anti-inflammatory substances, coronary dilators, cerebral dilators, peripheral vasodilators, anti-infectives, psychotropics, antimanics, stimulants, gastrointestinal agents, sedatives, antidiarrheal preparations, anti-anginal drugs, vasodilators, anti-hypertensive drugs, vasoconstrictors and migraine treatments, antibiotics, tranquilizers, antipsychotics, antitumor drugs, anticoagulants and antithrombotic drugs, hypnotics, anti-emetics, anti-nauseants, anticonvulsants, neuromuscular drugs, hyper- and hypoglycemic agents, thyroid and antithyroid preparations, diuretics, antispasmodics, uterine relaxants, mineral and nutritional additives, antiobesity drugs, anabolic drugs, erythropoietic drugs, antiasthmatics, cough suppressants, mucolytics, antiuricemic drugs, and mixtures thereof.

The pharmaceutical compositions contemplated herein are particularly well suited for use when it is desired to disperse medicaments in aqueous liquids and/or to cover the undesirable tastes possessed by many pharmacologically active ingredients. Examples of such materials include acetaminophen and other bitter medicaments. The medicament is generally mixed with maltodextrins and a flavoring agent and/or a sweetening agent and the mixture is melt-spun to obtain the pharmaceutically active product with the flavor of unpleasant medicaments masked.

It has been found that when antigens or antibodies are processed with maltodextrins according to the present invention, a matrix product can be produced which has considerably improved dispersibility in water. Thus, a powdered antibody or antigen composition having high dispersibility in water can be prepared which can be prepared for delivery systems such as shakes consumed for treatment of gastrointestinal problems.

One embodiment of the present invention also includes cosmetic products, i.e., those products which include ingredients having cosmetic activity. Such products can e used for treating hair or skin cosmetically. The active ingredient can be included (1) within the matrix, (2) outside the matrix, or (3) be incorporated in the product both inside and outside the matrix. A non-limiting list of ingredients which have cosmetic activity includes mucopolysaccharide, biotin, nicotinamide compounds, sun screen such as para-aminobenzoic acid, hair conditioner, and combinations thereof.

One class of food products according to the invention is improved soup mixes. These materials are frequently prepared from various dehydrated components which are packaged to protect them from ambient moisture and/or humidity. These mixes generally are unable to support significant quantities of oleaginous components because of the incompatibility of the oleaginous material with the dehydrated component, the difficulty of dispersing oleaginous components in aqueous media, and the need to know the soup mix readily handled so that it is a relative free-flowing powder rather than a paste, as would be the case if it were combined with large quantities of fats or oils.

The saccharide-based matrices of the present invention overcome the prior art difficulties by making it possible to combine both a fat and/or oil component with conventional soup mix ingredients. The resulting product according to this invention is readily dispersible in hot or warm water, just as is the conventional or basic soup mix; but with the incorporation of the oleaginous component, it has a much richer flavor and an improved, full-bodied mouth feel. Thus, the organoleptic properties of the soup prepared from the compositions of this invention are greatly improved.

One type of soup mix according to the present invention comprises maltodextrins, an oleaginous component and a soup base component. The oleaginous component can be a conventional edible glyceride, fat or oil. In general, the oleaginous component is an animal fat such as tallow, lard, or hydrogenated animal and/or vegetable oils, such being solids at normal room temperature. In certain desirable embodiments of the invention, the oleaginous component is an unhydrogenated or lightly hydrogenated vegetable oil such as corn oil, canola oil, cottonseed oil, sesame oil, grape seed oil, sunflower seed oil, rapeseed oil peanut oil, and like oils. The soup base component can be widely varied depending upon the particular flavor and type of soup. Some soups, such as split pea, are relatively thick and heavy, while others, such as vegetable soup or broth, are much thinner and lighter in texture and taste. Accordingly, the soup base can comprise meat and meat extract components, vegetables, starches, extracts, spices, herbs, thickeners, and the like. An additional advantage of the use of maltodextrin matrix soups according to the present invention is that they have a good full rich mouth feel without the use of large quantities of oleaginous substances or thickeners.

Incorporating soup mix in the novel matrix of this invention can preclude the use of soup bases containing large pieces of material such as noodles, meat chunks, vegetable slices, and the like. The organoleptic perception to the consumer of the soup base is the same as a soup base which includes large particles. Moreover, the resulting melt-spun corn syrup solids-containing product can be used in conjunction with large solid materials to enhance the organoleptic qualities. The advantages of superior taste, richness and mouth feel can still be obtained.

The mixture to be melt-spun in the preparation of soup mixes generally contains from about 0.1 to 90 percent maltodextrin solids, from about 0.1 to 35 percent oleaginous component, from about 20 to about 70 percent of the soup base component, and from zero to about 3 percent licithin. Preferably, the mixtures contains from about 29 to 8 percent maltodextrins, from about 8 to 35 percent oleaginous component, from about 20 to 60 percent of the soup base component, and from zero to about 3 percent lecithin.

Related products prepared according to the invention are gravy and white sauce mix compositions. While these are generally prepared in the same manner as the soup mixes, gravies include meat extracts, protein hydrolysates and the like. White sauces, similarly prepared, contain flour and dairy components, giving the sauces their distinctive flavor and properties. Here again, the use of maltodextrins assists in dispersing the ingredients in aqueous mixtures and in giving a rich mouth feel.

Another product made possible through the technique of the invention is a saccharide-based matrix containing a thickener. The thickeners useful for the invention are comestible thickeners useful for thickening food products such as soups, gravies, and sauces. Such thickener include, among others, cornstarch, flour, gelatine, pectin, gums, hydroxyethyl cellulose, hydroxypropylmethyl cellulose and carboxymethyl cellulose. Thickener compositions according to the invention have been prepared using between about 10 and about 650 percent thickener, between about 36 and about 90 percent corn syrup solids, and between 0 and about 9 percent sorbitol. Sorbitol is an ingredient which may be added to compositions containing thickeners to prevent blow-by of powdered thickener and to ease processing and reduce burning of certain thickener mixtures processed according to the invention. Other similar ingredients include mannitol and xylitol. One of the advantages of these compositions is that the flakes or other matrix containing the thickeners readily disperse in water, avoiding the clumping observed when such thickeners are added to foods in conventional ways. The thickeners retain their capacity to thicken the liquid comestibles to which they are added.

Another product uniquely available according to the claimed invention is flaked or granular nut paste, such as peanut butter. Peanut butter compositions according to the present invention have been made from the maltodextrin feedstock having a D.E. between 34 and 38, peanut butter, and, optionally, an additional oleaginous component. The solid peanut butter products are in themselves tasty. This is attributable in part to the extremely fine dispersion of the nut material which occurs during the flash flow process, allowing greater accessibility to the flavor elements of the nut than has heretofore been possible. The solids also have a variety of uses in the culinary and confectionery arts. One example is the use of the peanut flakes and granules of this invention to flavor salads and vegetables or other esculent materials. In the confectionery art they are well adapted for use in the preparation of chocolate confections to which the products of this invention lend a strong, rich peanut flavor. Among the advantages of the flaked product is that when it is used as a flavorant, it allows the use of relatively small amounts of nut matter because of the conversion of the nut matter and delivery-enhancing quality of the flash flow process. The product is also advantageous from the nutritional standpoint, allowing nut protein as well as nut oil to be used. As a side advantage, the combination of nut proteins and nut oil provides a flavor closer to that of the genuine net feedstock. This also provides certain economic advantages because separation of the nut oil, the conventional nut flavor component used in processed foods, from the nut protein is not required; the whole nut may be used.

A particularly desirable flake product has been found which is made by processing a combination of hazelnut paste and peanut paste with maltodextrins. This flake is especially useful as a spread, or a soft-serve ice cream additive, or a candy center. Other applications of this flake to produce food products will be readily discerned by the skilled artisan, and the scope of the present invention is intended to include all such other applications.

Another method of producing a reduced-fat nut composition is disclosed in U.S. Pat. No. 5,079,027 to Wong et al. The method and composition disclosed in the Wong et al '027 reference includes de-fatting roasted and ground nut solids, followed by grinding the solids to a particle size of predominantly less than 18 microns and then smearing the nut solids to reduce the amount of cytoplastic reticuli. This is a very high-energy process to provide a low-fat product. The present invention reduces the amount of energy required to obtain a de-fatted nut product and is, therefore, a significant improvement over the Wong et al '027 method. Moreover, the present invention can be used to further improve a nut product by using the nut product of Wong et al as the nut constituent in the feedstock which is subjected to flash flow. The resulting matrix will be a nicely-bulked, high-intensity flavor, very low-fat nut product.

Optionally, nut matrix (e.g., flakes) may be combined with water or other liquid media to "reconstitute" the nut matrix to a paste form having a consistency similar to that of the original nut butter. Such "reconstituted" pastes possess several advantages, among them that the nut material (oil and protein) has been bulked by incorporation into the matrix without loss of high-quality flavor characteristics. This allows the production of a larger quantity of nut-flavored medium than otherwise possible. Furthermore, because the nut oil content in a given volume of paste is reduced significantly from the oil content in nut paste, the product of the present invention is lower in fat and calories than nut past. Additionally, because of the extraordinarily fine dispersion of converted nut material, the organoleptic qualities of the nut are retained and/or enhanced, producing a flavorful expanded product.

For example, nut-based flakes can be used as an ingredient to make soft-serve ice cream. The nut-based flakes can be used in, or together with, a dry mix and added to water just prior to use as a soft-serve ice cream. Alternatively, the nut-based flakes can be added to an ice cream liquid mix just before use in a soft-serve ice cream machine (freezer). The nut flake of the present invention provides rapid dispersion, which enhances its use for making ice cream.

As with other products according to this invention, a homogeneous mixture of maltodextrins and peanut butter was prepared. The mixtures may contain an oleaginous component such as corn oil, for example, to provide a richer flavor, and sweeteners such as honey, sugar, and the like. The peanut butter compositions according to the present invention contain sufficient glucose-bearing saccharide to act as a carrier. Such compositions generally include from about 20 to about 70 percent maltodextrin feedstock having a D.E. of from about 34 to 38, from about 80 to about 30 percent peanut butter, up to about 20 percent of an oleaginous component, and from about zero to about ten percent of a sweetener. The preferred compositions include from about 30 to about 70 percent of the maltodextrin feedstock and from about 70 to about 30 percent peanut butter. Some also include oleaginous component and/or a quantity of sweetener.

A preferred product may be produced from a saccharide-based matrix composed of 50 parts peanut butter and 50 parts corn syrup solids by adding water to produce a nut cream having 18 percent added water content. Many other nuts are useful in accordance with the invention, including, but not limited to, almonds, hazelnuts, pecans, cashews and macadamia nuts. A most preferred embodiment of the nut paste aspect of the present invention is a reconstituted nut butter or cream which has been prepared by combining a peanut matrix of 50% peanut butter and 50% maltodextrin (D.E. 36) with low-fat milk (2% fat milk). the resulting product has a viscosity which is very stable over a period of time, e.g, up to three weeks. It has been found that the reconstituted product should be prepared by addition of liquid, e.g., water, 2% milk, skim milk, chocolate sauce or syrup, in an amount of from about 10%–25% liquid in the final product. A present preferred embodiment has a water or reduced-fat milk content of 18%. Preparation of a nut-bearing matrix as a confections or a confectionery ingredient can include introduction of chocolate as part of the feedstock. Thus, the feedstock would then include maltodextrin, nut paste, and chocolate (as a solid, syrup or liquid).

Another product according to the present invention is a ready-to-use mustard. This novel product is well-suited for use in food preparation, including salads and sandwiches, and as a condiment on ham, beef, and other meat products. The mustard product has been prepared by making a mixture of maltodextrin feedstock having a D.E. of between 34 and 38, mustard base, and any desired adjuvants, melt-spinning the mixture so formed, and recovering the solid melt-spun product. As used herein, the mustard base includes mustard or ground mustard seed and can also include the adjuvants used in the manufacture of prepared mustard.

These mustard adjuvants include vehicles such as acetic acid, mustard oil, and other oils and spices such as tumeric and the like. The mustard adjuvants are desirably combined with ground mustard seed and the ingredients are combined into a homogeneous mixture. The mustard component is combined with the maltodextrin and the combination is then melt-spun. The resulting solid material recovered from the melt-spinning is, in effect, a dry stabilized mustard product. It is readily used by combining it with meat, poultry, salad ingredients, vegetables, and the like to provide a mustard flavor. It can be used in prepackaged, ready-to-eat foods, or it can be used as a condiment on salad and the like, as set forth herein.

A further product according to the present invention is a ready-to-use catsup. This novel product is well suited for use in food preparation, including salads, sandwiches, eggs, and vegetables, and as a condiment on ham, beef, and other meat products. The catsup product is prepared by making a mixture comprising maltodextrin and a tomato base or catsup, melt-spinning the mixture so formed, and recovering the solid melt-spun product. As used herein, the catsup base includes tomatoes or a tomato product such as tomato paste and can also include the adjuvants used in the manufacture of prepared catsup.

These catsup adjuvants include vehicles such as water, spices such as salt, onions, garlic, natural and artificial flavors, and sweeteners such as corn syrup, sucrose, dextrose and the like. It will be understood by those skilled in the art that the adjuvants can be added in a number of forms; thus, onion powder, onion oil, or a combination thereof can be used. The catsup adjuvants are desirably combined with the tomato component, and the ingredients are combined into a homogeneous mixture. The catsup component is combined with the maltodextrin feedstock and then melt-spun. The resulting solid material recovered from the melt-spinning is, in effect, a dry stabilized tomato catsup product. It is readily used by combining it with meat, poultry, salad ingredients, vegetables and the like to provide a catsup flavor. It can be used in prepackaged, ready-to-use foods, or it can be used as a condiment on salad and the like, as set forth herein.

Another esculent material readily prepared according to the present invention is a mayonnaise-like product which uses much less amounts of oil than conventional products. The key to the preparation of such materials is the use of the maltodextrin matrix of the present invention with oil in melt-spun form. A mixture is prepared to contain maltodextrin feedstock and vegetable oil oleaginous component. The vegetable oil can be a natural or very lightly-hydrogenated vegetable oil such as corn, soybean, sunflower seed, cottonseed, rapeseed (canola), sesame, grapeseed or like oil. The maltodextrin feedstock and oil is then melt-spun, and the solid product is recovered. For this embodiment of the invention, the feedstock is generally present in an amount greater than the oleaginous component. The quantity of oleaginous material should be sufficient to provide a reasonable quantity of oil in the recovered solids, but it should not be enough to cause the solids to become patently oily. In general, the oleaginous component should comprise from about ten to about 40 percent of the melt-spun material.

The mayonnaise-like product is prepared by beating egg yolks and adding the saccharide-based product resulting from the maltodextrin solids with the oleaginous component. This mixture is then flavored with salt, mustard, vinegar, citrus juice, and the like. In addition to the foregoing flavor constituents, other conventional ingestibly-acceptable ingredients can be used, including vehicles such as water and preservatives and/or antioxidants such as calcium disodium ethylene diamine tetracetic acid and butylated hydroxy-anisole and the like. The result is a very appetizing mayonnaise-like food which can be used in all instances where mayonnaise or salad dressing is used. The advantage of this product is its lower fat content.

It will be appreciated by those skilled in the art from the present description that products other than esculent products can e prepared with the maltodextrin material of the present invention. For example, a cosmetic composition can be prepared to contain an oil-soluble material such as fragrance materials, perfumes, sun screens, topical medicaments and the like.

In another embodiment of the invention it is possible to incorporate gelling agents such as xanthan and other gums in the saccharide-based matrix product. Examples of suitable gelling agents include materials such as xanthan gum, guar gum, carrageenan gum, gum tragacanth, pectin, alginates (e.g., solid alginate), gum karaya, locust bean gum, gum acacia, agar gum, cellulose gum mixtures thereof and the like, as well as other food gels known in the art. Gelling compositions have been prepared with maltodextrin feedstock having a D.E. of from about 34 to 38 and a gelling agent such as xanthan gum, melt-spinning the mixture, and recovering a solid product. The quantity of gelling agent in the composition should be sufficient to provide the necessary gelling. On the other hand, the agent must be incorporated into the matrix so that it is held until ready for use. It is desirable in certain embodiments that the gelling compositions according to the invention contain from three to 40 percent, and preferably 5 to 20 percent, of the gelling agent, with the remainder substantially being maltodextrin or, preferably, corn syrup solids.

In a further embodiment of the present invention, the gelling composition may further incorporate a sugar therein in addition to the maltodextrin and the gelling agent. It has been surprisingly discovered that a saccharide-based matrix incorporating maltodextrin, a gelling agent, and sugar is instantaneously dispersible, i.e., capable of dissolving or dispersing over a period of a few minutes, in aqueous liquids to be gelled. Such instantaneous dissolving provides the matrix with enhanced properties over known gelling compositions in that the gelling composition is easily incorporated into solution without the need for stirring or mixing or use of wetting agents. Additionally, by accomplishing an instantaneous dispersion without the need for mixing, the novel gelling compositions can be used to efficiently prepare a uniform gel which does not exhibit water separation.

As the term is used herein, "sugars" refers to mono- and disaccharides other than maltodextrin, corn syrup solids, and polysaccharides, which are added to the compositions primarily for their sweetness or flavor characteristics. In contrast, maltodextrin is a fermented product which is much less sweet, as well as less hydroscopic than the "sugars" herein utilized. A non-limiting list of useful sugars as an additional component to be processed with the maltodextrin and the gelling agent includes sucrose, fructose, dextrose, mannitol, sorbitol, glucose, lactose, maltose and the mixtures thereof. Preferably, the added sugar is included in the matrix in amounts from about 2 to about 35 percent, more preferably from about 5 to about 30 percent, and most preferably from about 10 to about 20 percent by weight of the matrix.

In use, the gelling composition of the invention is, for instance, dispersed in water or an aqueous liquid. Gelling agents or gums are commonly available as fine non-agglomerated powders and are frequently difficult to dissolve or disperse in the liquid to be gelled. Alternative preparations of these agents are agglomerated, producing greater, although inefficient, dispersibility. Conventional dispersions of these gelling agents often employ wetting agents such as propylene glycol or oils. The novel melt-spun gelling compositions according to the invention, however, readily disperse and enter solution without prolonged or excessively vigorous mixing and without the need for wetting agents. Moreover, the alternate embodiment involving the matrix incorporating maltodextrin, a gelling agent, and an added sugar is instantaneously dispersible and, as such, instantaneously enters into solution upon contact with aqueous medium.

Aqueous systems, including gelling compositions, in accordance with the invention possess additional advantages over conventional preparations. Among these advantages are improved consistency and higher viscosity of gels formed from melt-spun gelling compositions. These compositions also possess a greater clarity than obtainable with conventional gels. The use of extremely fine gel dispersion in the maltodextrin matrices of the present invention prevents syneresis, i.e., separation of water from the gel. It is believed that this phenomenon reduces the amount of free water available for growth of microorganisms such as bacteria in the gels. Thus, gels formed in accordance with the present invention are more suitable for use in food products where preservation of the products is desirable.

For example, aqueous systems of melt-spun compositions comprising a gelling agent-bearing matrix may be injected into processed meat products such as hams or turkey breasts to produce expanded meat products. Upon gelling, the dispersions act as bulking agents and, by trapping excess water, improve the shelf life and spoilage resistance of the products. For these types of products, various gums are useful, as described above. The preferred gelling agent, however, is κ carrageenan. To produce these expanded meat products, an aqueous dispersion of a κ carrageenan-containing melt-spun composition is commonly pumped into the meat. For example, the dispersion may contain κ carrageenan present in the melt-spun composition as one part carrageenan to three parts maltodextrin (D.E. 42). The treated meat is then heated, thereby inducing the gelling of the carrageenan, producing a bulked meat product. The proportion of gelling agent in the melt-spun compositions useful for these products may range from about 0.5 to about 60 percent, and more preferably from about 30 to about 50 percent. Most preferably, the gum is present in an amount of from about 35 to about 38%.

Another example of a highly useful product which includes maltodextrin and gums is in the area of x-ray contrast media. A contrast medium is ingested to provide enhanced x-ray images. Barium sulfate ($BaSo_4$) is a well known contrast medium. It is important to optimally disperse the medium in the targeted part of the anatomy to obtain the best images. Barium sulfate can be optimally dispersed by producing, e.g., by spinning, the $BaSo_4$ with maltodextrins and gums to produce a matrix in accordance with the present invention. The matrix can then be mixed with water to provide an aqueous medium for ingestion by the patient. The gums/maltodextrin/$BaSo_4$ combination provides a high viscosity medium which has excellent coating and adherence to the internal surfaces of, among other organs, the esophagus and the stomach lining. Moreover, the $BaSo_4$ is substantially consistently dispersed throughout the medium for even and sharp contrast. The combination is excellent as an opaque medium for gastrointestinal radiography.

A large variety of other products requiring gels may e produced using aqueous suspensions of the melt-spin maltodextrin gum compositions of the invention. For example, by including a volatile fragrance in the product, gels suitable for use as air fresheners may be created. In such products the improved consistency and increased viscosity of the gels possible using the process of the invention are advantages that are readily apparent. The gelling compositions may also be used to replace conventional products in various foods such as frozen desserts and soups, gravies and sauces, and the like.

In yet another embodiment of the invention, it is possible to incorporate into the saccharide-based matrix product emulsifiers such as those used in edible products, especially baked goods. A non-limiting list of such emulsifiers include mono-and diglycerides of fats, oils and fatty acids, propylene glycol esters of fats, lactylated fatty acids, polysorbates, polyglycerol esters, ethoxylated mono- and diglycerides, lecithin and the like, and mixtures thereof.

In one preferred embodiment it has been found that polyglycerol esters can be made sufficiently soluble for inclusion in dough products such as cakes, breads, etc. This has proven particularly useful in reducing or eliminating the fat content of dough products because the polyglycerol esters provide aeration of the dough for baking, thereby reducing the fat content in dough which usually provides the aeration. For example, polyglycerol ester emulsifier sold under the trademark SANTONE®, by Van Den Bergh Food Ingredients Group, is generally not sufficiently soluble for dissolution and mixing into dough ingredients. When SANTONE® grand emulsifier is processed with maltodextrin in accordance with the present invention, however, it has been found to be quite soluble and readily mixed with other ingredients to form a dough product. Moreover, baked goods prepared from matrix-bearing dough retain the aeration characteristics of dough prepared using a full complement of oleaginous (fat) substance.

In still another embodiment of the invention, flavor oils and essences may be included in the saccharide-based matrix. While these oils are generally derived from plant extracts, they may alternatively be synthetically derived. Peppermint oil, spearmint oil, cinnamon oil, oil of wintergreen, citrus oils and other fruit essences are the most commonly used flavor oils which are employed in the present invention. Flavor oils such as peppermint oil, spearmint oil and cinnamon oil are particularly harsh and create a burning sensation in the mouth if ingested in too high a quantity. The present invention allows for the use of minimal quantities because of the ability to combine very small amounts in a bulk delivery vehicle, i.e., the maltodextrin matrix. The micronized dispersion gives the perception that a greater quantity of flavor is present than the actual amount, thereby enhancing both the organoleptic impact with less flavor oil and eliminating the need for higher amounts. Moreover, the possibility of unwanted "hot spots" of intense flavor is virtually eliminated. This is particularly useful in applications such as chewing gum compositions, where the addition of flavor oil at high concentrations to achieve a more intense flavor impact results in plasticization of the gum base components and sloppy chew characteristics.

Examples of citrus or first oils and/or essences which are useful include a host of materials such as apple, apricot, banana, blueberry, cherry, grape, grapefruit, lemon, lime, orange, pear, peaches, pineapple, plum, raspberry, strawberry and the like. Mixtures and derivatives of these oils are contemplated.

Additional flavoring agents may be chosen from synthetic flavor oils and flavoring aromatics and/or oils, oleoresins and extracts derived from plants, leaves, flowers, fruits and so forth, and combinations thereof. For example, clove oil, bay oil, anise oil, eucalyptus oil, thyme oil, cedar leaf oil, oil of nutmeg, oil or sage, oil of bitter almonds, and cassia oil may be used. Commonly used flavors include menthol, artificial vanilla, cinnamon derivatives, and various fruit flavors, whether employed individually or in admixture.

Flavorings such as aldehydes and esters may also be used, including cinnamyl acetate, cinnamaldehyde, citral diethylacetal, dihydrocarvyl acetate, eugenyl formate, p-methylamisol, and so forth. Generally, any flavoring or food additive may be used, such as those described in *Chemicals Used in Food Processing* (National Academy of Sciences, 1274), pp. 63–258.

Further examples of aldehyde flavorings include, but are not limited to, acetaldehyde (apple); benzaldehyde (cherry, almond); anisic aldehyde (licorice, anise); cinnamic aldehyde (cinnamon); citral, i.e., alpha citral (lemon, lime); neral, i.e., beta citral (lemon, line); decanal (orange, lemon); ethyl vanillin (vanilla, cream); hellotropine, i.e., piperonal (vanilla, cream); vanillin (vanilla, cream); alpha-amyl cinnamaldehyde (spicy fruity flavors); butyraldehyde (butter, cheese); valcraldehyde (butter, cheese); citronellal; decanal (citrus fruits); aldehyde C-8 (citrus fruits); aldehyde C-9 (citrus fruits); aldehyde C-12 (citrus fruits); 2-ethylbutyraldehyde (berry fruits); hexenal, i.e., trans-2 (berry fruits); totyl aldehyde (cherry, almond); veratraldehyde (vanilla); 2,6-dimethyloctanal (green fruit); and 2-dodecenal (citrus, mandarin); cherry; grape; strawberry shortcake; mixtures thereof; and the like.

Other specific flavor compounds such as ethyl acetate, thiophene, ethyl propionate, ethyl butyrate, 2-hexanoate, 2-methylpyazine, heptaldehyde, 2-octanone, limonene, and eugenol are also useful.

The flavorant oil content of the present delivery systems is generally in the range of about 0.02% to about 40% by weight of the delivery system. Deviations from this range are certainly possible provided the micronized dispersion of the oil in the matrix results from the flash-flow process. Preferably, the oils are present in amounts of about 0.5 percent to about 20 percent by weight of the delivery system and most preferably about 2 percent to about 12 percent.

The present invention is used to particular advantage with oleoresins. Oleoresins now form an important source of flavoring in a wide spectrum of food products because they are free from many of the inherent disadvantages of ground spices. In particular, they are hygienic and can be standardized for flavor quality and strength to within acceptable limits by blending of the essential oil and resinous fractions. Unlike the essential oils, these extracted products contain any natural antioxidants which may be present in the original spice, a valuable attribute when they are used in the seasoning of meat products, where the red color of the end-product is of importance. With certain exceptions (e.g., oleoresins of dill, celery, cumin and paprika), they have a very good shelf life and retain their color and flavoring powder for long periods if stored in a cool place in well-closed containers. The exceptions are those spices which contain high percentages of fixed oils which tend to oxidize and become rancid.

While there are advantages to the use of oleoresins in food products, certain problems arise. Oleoresins are concentrated and are from 10 to 50 times stronger than the spice itself. In conventional uses, this necessitates the weighing of small quantities of the oleoresin. As a result, the amount remaining in a weighing vessel may significantly affect the level of flavor in the end-product. Furthermore, depending on the spice and the solvent used, the resulting oleoresin may vary in physical form from a light, mobile oil (e.g., oleoresin coriander) through a viscous paste (e.g., oleoresin Dalmatian sage) to a friable solid (e.g., oleoresin tumeric). Such products cannot readily be incorporated directly into food mixes without the danger of local concentrations or "hot spots."

As a source of flavoring, therefore, the spice oleoresins are valuable in modern food processing. Because of their power effects, however, it is necessary to dilute them prior to incorporation into a product mix. This is achieved by persons having ordinary skill in the art through the use of one of liquid or dry powder products such as essences, emulsions, solubilized spices, plated dispersions, or encapsulated spices. Each of these products has marked advantages in usage over the equivalent ground spices, the essential oils, or the oleoresins, although none is entirely free from disadvantages in meeting the demands of processing and storage. A description of conventional knowledge of oleoresin technology is provided, for example, in Heath, *Flavor Technology: Profiles, Products, Application* (London: AVI Publishing Co., Inc.). None of the previous technology exhibits the advantages of the maltodextrin matrices when used to delivery oleoresins. The flash flow technology produces extremely fine dispersions of the materials in the feedstock and, as a result, oleoresin-containing matrices are devoid of hot spots, possessing a highly uniform distribution of the intense oleoresin flavor and providing an even, rounded, and easily-controllable means of flavoring foods.

In another embodiment of the invention, matrix compositions containing a low-sweetness, low-calorie content such as maltodextrin and a sweetener exhibit advantages over conventional mixtures of carriers and sweeteners. Especially efficacious are compositions which include a maltodextrin carrier with one or more "super sweeteners," i.e., sweeteners having perceptible sweetness per unit weight greater than that of sugar. Among these super sweeteners are included, without limitation, aspartame, cyclamates, saccharin, and Sucralose®. Such matrix compositions may optionally include sorbitol or an oleaginous material in the feedstock to aid in limiting blow-by of the sweetener during the flash-flow process.

Because of the intense sweetness of the super sweeteners, they are commonly bulked before use by means of the addition of conventional bulking agents. The matrix compositions of the invention provide a uniformity and a fineness of dispersion of the super sweetener which is better than can be achieved by the mixing or blending processed used in conventional commercial food preparation. The matrix composition may also be used to achieve intimate mixtures of super sweeteners which provide a synergistic sweetness effect. For example, sucralose and aspartame can be effectively combined even though Sucralose® is a liquid.

The flash shear and flash heat processes achieve a more uniform distribution of the super sweetener due to the flow pattern of the composition being processed. Furthermore, the super sweetener is, in effect, annealed to the carrier, thereby preventing the settling of the super sweetener from the carrier during shipping and handling that is commonly observed with conventional mixtures. The skilled artisan will also appreciate that the relatively low processing temperatures used for the flash flow technique permit the use of heat sensitive sweeteners such as aspartame in the matrix product. Similarly, many other types of heat-sensitive ingredients, both comestible and pharmaceutical, can likewise be used without degradation during processing.

The matrix compositions of the super sweeteners are also advantageous in baking as compared to the use of the artificial sweeteners alone. This may result from the matrix compositions more closely mimicking sucrose during the baking process, the corn syrup solids provide the bulk and other properties associated with sucrose. Also, the bulking character of the carrier can be taken advantage of to produce matrix sweetener products which are equivalent, on a spoon-for-spoon basis, with sucrose.

Optionally, the super sweeteners in a matrix composition can be incorporated with oils to achieve delays in sweetness or to achieve specific sweetness effects on the tongue, especially when the oil is in a fine colloidal form, i.e., in droplets on the order of 1–20 microns in diameter.

It will be understood by those skilled in the art from the present description that additional adjuvants can be included with the maltodextrins and other functional ingredients. Thus, colors, dyes, pigments, antioxidants, antifungal agents, preservatives, cosmetics and such can be added to improve the appearance, aroma, shelf life, or other properties of the products prepared herein. When an esculent or pharmaceutical product is involved, it will be understood that the product contains other adjuvants which are particularly suited for the end use.

When maltodextrin feedstocks are melt-spun according to the present invention, a solid material results. It is frequently in the form of flake-like particles, the size of which varies according to the material and the process conditions. Under some processing conditions, the solid product formed will vary from particulate to floss-like. With some mixtures, higher processing temperatures produce a flake-like material; with others, a particulate material is obtained at the higher temperature.

EXAMPLES

The following examples serve to provide further appreciation of the invention, but are not meant in any way to restrict the effective scope of the invention.

Example 1

Samples of feedstock, e.g., two maltodextrins identified as "Maltrin" M365 (D.E.=36) and "Maltrin" M255 (D.E.=25), made by Grain Processing Corporation, Muscatine, Iowa, were prepared by reducing agglomerations of the maltodextrins to a free-flowing solid powder. Each material was introduced to a melt-spinning apparatus having an open circular spinning head with a diameter of about 5.5 inches traveling at a rotational velocity of from about 3400 to about 3600 r.p.m. and melt-spun at low temperature to provide white flakes.

Under these conditions the material was flung instantaneously against the inside surface of the spinning head, which has been provided with a heat "ribbon." The heating ribbon was maintained at a relatively low temperature of from about 130° C. to about 180° C. for flash-heating the maltodextrin feedstock. Unlike previous attempts to melt-spin maltodextrins at cotton candy spinning conditions, a solid white matrix material was produced which possessed a physical and chemical structure different from the feed stock. A table has been set forth below which reports the conditions for producing the inventive matrix.

| EXAMPLE 1 | | | |
|---|---|---|---|
| FEEDSTOCK PRODUCT | RIBBON TEMPERATURE | RPM* | RESULTING MATRIX |
| SUGAR | 200° C. | 3600 | FIBERS |
| SUGAR WITH REDUCING SUGAR (LACTOSE) | 210° C. | 3600 | FIBERS |
| REDUCING SUGAR (LACTOSE) | 224–229° C. | 3600 | FLOSS |
| MALTODEXTRIN (D.E. 20) | 200° C. | 3600 | UNUSABLE |
| MALTODEXTRIN (D.E. 34–38) | 165° C. | 3600 | CHIP OR FLAKE |
| MALTODEXTRIN (D.E. 25) | 140° C. | 3600 | CHIP OR FLAKE |

*SIZE OF SPINNING HEAD IS 5.5 INCHES; HEAD OPENINGS ARE SLITS WHICH ARE 3–5 MM LONG BY 0.5–0.75 MM WIDE.

The inventive flakes and/or chips were contacted with an aqueous medium and found to dissolve in what appeared to be a true solution.

Simply stated, a non-sucrose, saccharide-based matrix possessing enhanced new physical and chemical properties resulting from flash-flow alteration cannot be achieved unless the feedstock and process conditions are carefully selected in accordance with the parameters of the present invention.

Unless otherwise noted, in the examples which follow the maltodextrin was "Maltrin" M365 (D.E.=36.5). In a number of the examples the maltodextrin was Maltodextrin 35R (D.E.=35), produced by A. E. Staley Mfg. Co., Decatur, Ill. For simplicity, the use of such material will be indicated by the following entry: "35R maltodextrin."

Example 2

A mixture of 89.9% (45.1 g) of maltodextrin D.E. 36 and 10.1% (5.1 g) of garlic oil was prepared. The garlic oil was obtained from Pent Mfg. Co., Fairfield, N.J. This mixture was processed in accordance with the present invention to produce uniform white flakes which provided an excellent bulking mass.

The flake product itself has a sweet taste which subsequently became perceived as a very strong garlic taste. When placed in water, it formed a colloid.

Example 3

A mixture was prepared by combining 38.4% (20.3 g) sifted "Knorr" soup mix and 37.9% (20.5 g) maltodextrins D.E. 36. To the resulting mixture 23.7% (12.5 g) of corn oil was added and the entire composition was mixed thoroughly. The mixture was then fed to the apparatus used herein.

The resulting material appeared as a substantially uniform particulate which as recovered from the spinning bowl and tested by contacting with warm water. The suspension was colloidal and excellently dispersed. The flavor system in this produce was very well rounded without organoleptic sharpness of any form. These results are attributed to the modifying effect of the oil in the product.

Example 4

A thorough mixture of 32.3% (16.4 g) sieved "Knorr" soup mix, 31.9% (16.2 g) maltodextrins D.E. 36, and 35.8%

(18.1 g) corn oil was prepared. The mixture was processed in accordance with the present invention to provide a particulate, spiculate product. There was also some free oil in the product.

This produce was dispersed in a cup of warm water and appeared to be colloidal. The flavor was excellent. Some surface oil appeared in the product, but it was evident that this system could tolerate a heavy load of oil. Indeed, this contained over 50% more oil than the product of Example 3.

Example 5

A mixture is prepared to contain 83% (12.5 g) maltodextrin D.E. 36 and 17% (25.5 g) corn oil. This mixture was processed in accordance with the present invention at a speed of about 3600 r.p.m. and at a temperature of about 140° C. The mixture spun at high temperature provides smaller flakes than that spun at low temperature. Both were usable as a food grade matrix material.

Example 6

A mixture was prepared containing 16.7% (8.4 g) acetaminophen (obtained from Sigma Chemical Co. of St. Louis, Mo.), 30% (15.0 g) corn oil, and 53.3% (26.7 g) maltodextrins D.E. 36. The mixture was processed with the present invention. The melt-spun product was a white particulate having a slightly bitter taste.

Example 7

A mixture was prepared containing 30% (15.1 g) maltodextrins D.E. 36 and 70% (35.1 g) raw peanut butter. The ingredients were mixed in a glass mortar. The mixture was then processed according to the present invention to produce a small particulate, soft, flake-like material. The product has a dry appearance and the flavor is very good. It will be noted that this example is made up of 30 percent maltodextrins, yet is capable of providing a product with excellent peanut butter texture and taste properties.

Example 8

A mixture was prepared with 79.6% (39.4 g) maltodextrins D.E. 36 and 20.4% (10.1 g) "Mazola" brand corn oil. The ingredients were mixed in a porcelain mortar. The resulting mixture was then processed at a low heat setting of 140° C. Surprisingly, the resulting solid product was in the form of small spicule-like flakes which formed a colloidal dispersion when added to water.

Example 9

A mixture was prepared by beating three egg yolks for three minutes and then adding 15 g of the product of Example 8 dissolved in the juice of one lemon (ReaLemon®) plus one teaspoon of salt and ⅓ teaspoon of mustard powder and two teaspoons of white vinegar. Thereupon, the mixture was beaten for three additional minutes. The result is a delicious mayonnaise without the use of the cup of oil called for by the recipe. The product has the appearance found to be typical of the colloidal or colloidal-like materials produced according to this invention.

It will be apparent to those skilled in the art that the present invention provides the capability of making foods with organoleptic properties providing a creamy mouth feel without the same amount of oleaginous component usually included.

Example 10

A mixture containing 20% (400 ml) canola oil and 80% (1600 g) 35R maltodextrin D.E. 34.5 was prepared by mixing in a food processor for 30 minutes. This blend was processed at a low temperature setting of about 140° C. Nevertheless, a high-quality solid chip produce was recovered which could easily be used in food products as a bulking ingredient and as a dispersing agent.

Example 11

A mixture was prepared to contain 90.8% (22.8 g) maltodextrin, 4.3% (1.1 g) aspartame ("Nutrasweet," from Searle Inc. of Skokie, Ill.), and 4.9% (1.2 g) corn oil. The ingredients were mixed by hand in a glass mortar. The mixture was then processed to produce a solid in the form of flakes and spicules. It was very sweet and pleasant tasting. The product thus provides a readily usable sweetener with improved organoleptic properties which is incorporated substantially uniformly in a bulking/dispersing agent.

Example 12

A mixture was prepared to contain 9.2% (4.6 g) Keltrol xanthan gum (obtained from Merck & Co., Rahway, N.J.), 81.8% (41 g) maltodextrins D.E. 36, and 9% (4.5 g) Mazola corn oil. These ingredients were mixed with a glass mortar. the resulting mixture was then processed in accordance with the present invention.

The product was a high-quality solid in the form of chips or flakes. A 1.1 g quantity of this product (containing about 0.1 g xanthan gum) is added to 25 g of warm tap water. The product quickly disperses but slowly dissolves and forma gelatin-like material.

As a comparison, 0.1 g of the same xanthan gum is added to 25 g of water in the same manner. It disperses very slowly. Accordingly, it can e appreciated that the product of the present invention provides a superior way to disperse xanthan gum for food use and for industrial uses. Xanthan gum has been spun at levels up to 40% of the melt-spun mixture.

Example 13

A mixture was prepared from 50% (25 g) of tomato extender (obtained from Deltown Chermurgic, Greenwich, Conn.), 25% (12.5 g) maltodextrins D.E. 36, and 25% (12/5 g) corn oil. The mixture was processed according to the present invention to provide a granular material capable of being easily added to food products.

The flavor of the original tomato extender is extremely spicy and astringent. The processed product retains a very astringent, spicy flavor with an added sweet note. When the product is suspended in warm water it appears to be colloidal and the aqueous product is extremely concentrated in flavor.

Example 14

A mixture was prepared from 49.8% (12.5 g) French's Homestyle Chicken Gravy Mix, 25.1% (6.3 g) maltodextrins D.E. 36, and 25.1% (6.3 g) corn oil. The mixture was processed by spinning at about 140° C. to produce a flake-like product.

Example 15

A mixture was prepared by combining 20% (10 g) black strap molasses and 80% (40 g) maltodextrins D.E. 36. The material was processed at a low temperature setting of about 140° C.

The feedstock readily spun without clogging the apparatus to provide a product in the form of dark brown chips with an excellent molasses flavor.

Example 16

A pharmaceutical was prepared to contain 10% (10 g) sucralfate (obtained from Orion Corporation, Espoo, Finland), 5% (5 g) xanthan gum, 5% (5 g) corn oil, and 80% (8 g) maltodextrins D.E. 36. The material was mixed with a mortar and pestle and processed in accordance with the present invention to provide a high quality particular product.

In its original form sucralfate is a white amorphous powder practically insoluble in water. However, when 10 g of the resulting product was placed n an aqueous medium, the material dispersed and provided a suspension which possessed a pleasing mouth feel and was substantially flavorless.

Example 17

A mixture was prepared to contain 4.948% (25 g) "Bonivita Brand" grape seed oil, 4.948% (25 g) cocoa butter, 4.948% (25 g) herbal fragrance, 84.117% (425 g) maltodextrins 35R D.E. 34.5, and 0.049% (0.25 g) FD&C blue dye dissolved in 0.99% (5 g) ethanol. The resulting mixture was processed at a temperature of about 140° C. and 35600 r.p.m.

The solid feedstock underwent flash-flow condition to produce a product in the form of blue flakes. About 25 g of the product placed in a bath full of water produces a pleasing bath water with a nice blue color, herbal scent and skin feel.

Example 18

A protein mixture was prepared to contain 57.9% (29 g) maltodextrin solids D.E. 36, 29.9% (15 g) whey proteins, and 12.2% (6.1 g) corn oil. This mixture was processed at about 140° C. to produce a flake-like product.

The product appeared to retain its color during processing and when suspended in water a resultng suspension appeared to be colloidal.

Example 19

A mixture was prepared to contain 70% (35 g) maltodextrins D.E. 36, 25% (12.5 g) casein, acid hydrolysate (obtained from Sigma Chemical Co., St. Louis, Mo.), and 5% (2.5 g) corn oil. This mixture was processed to provide a light ten flake. When suspended in water, the flake appeared to form a colloidal dispersion.

Example 20

A mixture was prepared with 10% (5 g) corn oil, 2% (1 g) carrageenan (obtained from FMC Corporation, Philadelphia, Pa.), and 88% (44 g) maltodextrin D.E. 36. The material was spun at a low temperature setting of about 140° C. to provide a flake-like material. When 10 g of this material was placed in 2 g of water, a thick colloidal dispersion was formed.

Example 21

A mixture was prepared to contain 25% (25 g) "Vaseline Brand" petroleum jelly from Cheseborough-Ponds Inc., Greenwich, Conn., and 75% (975 g) corn syrup solids. This mixture was processed at 140° C. to produce a product in the form of white flakes which formed a colloidal dispersion when placed in warm water.

Example 22

A mixture was prepared to contain 50% (25 g) "Pillsbury" flour equilibrated at 100% relative humidity and 50% (25 g) maltodextrins. The mixture was processed satisfactorily to produce a product somewhat dry which appears as a small "puffed" flake.

Example 23

A mixture was prepared to contain 48.9% "Pillsbury" flour, 29.1% maltodextrins, 9.8% corn oil, 9.8% water, and 2.4% lecithin. The mixture was subjected to flash-flow conditions to produce an oily granular material which disperses in water.

Example 24

A mixture was prepared to contain 58.5% sieved "Knorr" soup mix, 29.6% maltodextrin D.E. 343.5, 9.2% corn oil, and 2.5% lecithin (Thermolec 68, obtained from ADM Ross & Rowe, Decatur, Ill.). The mixture was processed according to the present invention to produce a particulate material in the form of spicules which dispersed readily in warm water.

Example 25

A mixture was prepared to contain 5% (5 g) cyanine dye and 95% (95 g) maltodextrins D.E. 36 and combined in a glass mortar and pestle. The mixture was processed in accordance with the present invention to produce a bright green flake that readily disperses and dissolves in water to form a bright green solution.

Example 26

A mixture was prepared to contain 20% (10 g) flurochemical (obtained from Lehn & Fink Products Group, Montvale, N.J.), 2% (1 g) Triton X 100 (obtained from Sigma Chemical Co., St. Louis, Mo.), and 78% (39 g) maltodextrins D.E. 34.5.

The material was processed to product a product in the form of flakes. When placed in water, a colloidal dispersion was formed.

Example 27

A medicament mixture was prepared to contain 10% (5 g) Allontoin, a skin ulcer therapeutic (obtained from Lehn & Fink Products Group) and 90% (45 g) of 35R maltodextrin D.E. 34.5. The Chemical Abstracts' names for Allontoin are (2,5-Dioxo-4-imidazolidinyl) urea; 5-ureidohydantoin; glyoxyldiureide; and cordianine; it is a product of purine metabolism. The material was mixed in a porcelain mortar and subjected to flash-flow processing in accordance with the present invention. The melt-spun product was in the form of flakes and formed a cloudy solution when placed in water. A similar amount of material which had not been processed would not go into solution when placed in water.

Example 28

A confection mixture was prepared to contain 60% (30.1 g) raw peanut butter, 10.1% (5.1 g) honey, and 29.9% (15 g) maltodextrins D.E. 36. This mixture was processed to produce a light granular powder having a pleasant flavor. The transformation of the physical form of the feedstock was quite dramatic.

Example 29

A mixture was prepared to contain 20% (10 g) permethyl from Lehn & Fink Products Group and 80% (40 g) 35R maltodextrins. The mixture was blended in a glass bowl and processed at a low temperature setting of about 140° C.

Example 30

A mixture was prepared to contain 0.5% (0.25 g) "Lysol" fragrance and 99.5% (50 g) 35 R maltodextrins D.E. 34.5. The mixture was blended for 3 minutes and precessed by subjecting it to flash flow conditions to produce a high quality white flake with a sweet, pleasant Lysol" fragrance. When placed in water the flakes dissolved to form a weak colloid.

Example 31

A mixture was prepared to contain 20% (10 g) amphomer from Lehn & Fink Products Group and 80% (40 g) maltodextrins D.E. 36. The material was mixed in a porcelain mortar and then precessed under flash flow conditions at the temperature setting of 140° C. The resultant produce was in the form of slightly off-white flakes.

Example 32

A mixture was prepared to contain 10% (5 g) sodium bromide and 90% (45 g) 35R maltodextrins D.E. 34.5. The powders were mixed in a mortar and processed by subjecting it to flash flow conditions.

The resultant melt spun product was in the form of white flakes.

Example 33

A mixture was prepared of 20% (10 g) d'Limonene (obtained from Lehn & Fink Products Group) and 80% (40 g) maltodextrins D.E. 36. The mixture was processed a talow temperature of about 140° C.

The resultant material was in the form of white flakes that dissolved in water to form a colloid.

Example 34

The mixture was prepared to contain 5% (1.5 g) Dantobrom RW (obtained from Lehn & Fink Products Group, 5% (2.5 g) corn oil, and 90% (45 g) maltodextrins D.E. 36. The ingredients were mixed using a porcelain mortar and pestle and subsequently processed under flash flow conditions. The melt-spun product was in the form of white flakes.

Example 35

A bath medicament mixture was prepared of 10% (1 g) "Quaker Oats" oatmeal, 5% (5 g) Gleason Lite mineral oil, 80% (80 g) 35R corn syrup solids D.E. 34.5, and 5% (5 g) Blue Meadow fragrance. The oatmeal was powdered by processing in a blender for about three minutes. The oil was added and mixed well in the blender. The blended material was transferred to a mortar, the fragrance and corn syrup solids were added, and the materials were worked with a pestle for about five minutes.

The mixture we then subjected to flash-flow conditions at low temperature, producing chips which dispersed well when added to water. The dispersal appeared colloidal and the solution provided a soothing feel and pleasant fragrance.

The produce provides a superior bath product with improved dispersion when added to water.

Example 36

A mixture was prepared with 10% (20 g) Gleason Lite mineral oil, 2% (4 g) "Charlie" fragrance from REVLON, and 88% (176 g) 35R maltodextrins D.E. 34.5. The materials were mixed with a glass rod for about 10 minutes, then processed in accordance with the invention, producing white chips which were set aside.

Another mixture was prepared containing 9.896% (20 g) cocoa butter, 1.979% (4 g) "Charlie" fragrance oil, 87.086% (176 g) 35R maltodextrins D.E. 34.5, 0.049% (0.1 g) MGFD plus C Blue #1, and 0.99% (2 g) Ethanol 95%. The blue dye was dissolved in the ethanol, all of the other ingredients were added, and the combination was mixed well with a glass rod for about 10 minutes. This mixture was also processed according to the invention at low temperature, producing blue chips.

Next, equal parts of the white and blue chips were mixed, producing a beautiful blue and white chi pattern bath oil product which dissolved rapidly in tepid water, producing a gorgeous blue colloidal bath water very comforting to the skin.

Example 37

A mixture was prepared from 88% (44 g) 35R maltodextrins D.E. 34.5, 2% (1 g) Gelcarin GP 379, a carrageenan powder (obtained from FMC Corporation, Marine Colloids Division, Philadelphia, Pa.), and 10% (5 g) corn oil ("Mazola") by mixing the dry ingredients with a glass rod and then adding to the oil, followed by thorough mixing with the glass rod. The mixture was then processed according to the invention at low temperature. A high quality flaky product was obtained.

The flakes were contacted with an aqueous medicament at room temperature and stirred until disperse. A colloidal dispersion was produced.

Example 38

In this example, 190 grams of Gatorade® lemon-lime flavored drink mix granules were combined with 90 grams of maltodextrin 35R D.E. 34.5, a product of the ADM Co., until a uniform mixture was obtained. Thereafter, a 10-gram quantity of Mazola® corn oil was geometrically added to the mixture using a mortar and pestle. This mixture was then spun at the medium setting of 3500 r.p.m. to produce yellow spicules having a crisp flavor and high impact.

Example 39

In this example, the procedure of Example 38 was repeated except that 150 grams of maltodextrin were combined with the same amount (190 grams) of Gatorade®. This additional amount of maltodextrin caused the spun product to take the form of larger chips rather than the spicules of Example 38. In addition, it was observed that less of the as-spun product stuck to the bin ring. The flavor impact of the chips was not adversely affected by the additional amount of maltodextrin.

| EXAMPLE 40 PROTEIN PRODUCT ENHANCEMENT MATRIX ||
|---|---|
| INGREDIENTS | WEIGHT % |
| MALTODEXTRIN D.E. 36 | 50–92 |
| OLEAGINOUS COMPONENT | 8–36 |

In the present example, the saturated fat component of a protein product has been significantly reduced by the use of a saccharide-based spun matrix. The spun matrix agent is the maltodextrin processed by flash flow in accordance with the present invention. The matrix is formed by combining a low amount of oleaginous material such as animal fat, or replacement such as canola oil, etc., at a percentage such that it is significantly reduced when compared to the oleaginous content of a fat-bearing protein product. The material is processed by subjecting it to flash flow conditions and recovering a flake-like particulate material which can then be introduced into a protein product such as hamburger, a soy patty, or other protein material. The recovered particulate admixes more efficiently with meat and other protein media than does the Alleghenies material alone.

The result is a significantly reduced saturated fat product which emulates the texture and mouth feel of a high fat content protein product. As a result of this unique combination, meat products can be processed to significantly reduce the fat content yet preserve the organoleptic qualities of the meat such as mouth feel, texture, and flavor. Further examples will be provided herein which show how the flavor can be added along with the oleaginous replacement matrix.

EXAMPLE 41
SPUN MATRIX IN GROUND BEEF

| INGREDIENTS | WEIGHT % |
|---|---|
| MALTODEXTRIN D.E. 36 | 80 GRAMS |
| CANOLA OIL | 20 GRAMS |

In this example the spun matrix was prepared by uniformly mixing the maltodextrin with canola oil. The mixture was spun at 3600 r.p.m. at 140° C. to produce large dry flakes. The flakes were mixed with ground beef in accordance with the table set forth below. Beef hamburger compositions set forth in the table were pressed in a 4-inch square hamburger press to form patties. The patties were fried over a medium gas heat for 5 minutes, surface dried on a paper towel, and analyzed. A three-inch diameter center plug was pressed in a two-stage potato press to extract liquids to determine liquid or juiciness content.

| PRE-FRIED WEIGHT | FRIED 3-INCH DIAMETER PLUG PRESSED WEIGHT | FRIED 3-INCH DIAMETER PLUG LIQUIDS' WEIGHT | RATIO OF SOLIDS TO LIQUIDS |
|---|---|---|---|
| 6.00 oz. | 2.25 oz. | 0.90 oz. | 40.0% |
| 6.00 oz. | 2.30 oz. | 0.80 oz. | 34.7% |
| 6.00 oz. | 2.40 oz. | 0.75 oz. | 31.2% |
| 5.50 oz. | 2.55 oz. | 1.10 oz. | 43.1% |
| 5.75 oz. | 2.60 oz. | 1.05 oz. | 40.4% |

The samples containing flakes and a correspondingly reduced amount of hamburger had higher weights of juice and residual pressed solids. Also, the ratio of liquids to solids in such samples is equal or higher than hamburger with 20% beef fat. The hamburgers containing flakes were about 20% thicker after frying than the fried hamburgers without flakes. Finally, the appearance, texture and mouth feel of the low fat hamburgers with the flakes were virtually identical to that of the high fat hamburgers.

EXAMPLE 42
HAMBURGER FLAVORANT MATRIX

| INGREDIENTS | WEIGHT (%) |
|---|---|
| MALTODEXTRIN D.E. 36 | 78.0 |
| CANOLA OIL | 20.0 |
| SPICES - INCLUDING SALT, BEEF FLAVOR, PEPPER GARLIC, AND ONION | 2.0 |
| TOTAL | 100.0 |

In this example a flavorant-containing matrix was prepared which is suitable for enhancing the flavor of hamburger. First, the spices were uniformly mixed and thereafter combined with the oil. The maltodextrins were added to the oil/spice mixture until a uniform mixture was obtained. The uniform mixture was processed at a low setting yielding a spicy, beef-flavored flake.

EXAMPLE 43
HAMBURGER FLAVORANT MATRIX

| INGREDIENTS | WEIGHT (GRAMS) |
|---|---|
| SACCHARIDE-MALTODEXTRIN 35R D.E. 34.5 | 67.0 |
| MEAT-FLAVORED VEGETABLE OIL | 30.0 |
| XANTHAN GUM | 1.0 |
| CARRAGEENAN | 1.0 |
| SPICES - INCLUDING SALT, LIQUID SMOKE, FLAVOR, PEPPER, GARLIC AND ONION | 1.0 |
| TOTAL | 100.0 |

A process similar to that set forth in Example 42 was undertaken to provide a hamburger flavorant-containing matrix. The vegetable oil was initially warmed to a liquid. The spices and xanthan gum were added to the oil and a uniform mixture was obtained. Finally, the maltodextrin was added and uniformly combined with the above ingredients. The resultant mixture was processed at a low setting and a while flake having a strong beef flavor was obtained.

EXAMPLE 44
SAUSAGE FLAVORANT MATRIX

| INGREDIENTS | WEIGHT (%) |
|---|---|
| SACCHARIDE-MALTODEXTRIN 35R D.E. 34.5 | 67.0 |
| MEAT-FLAVORED VEGETABLE OIL | 30.0 |
| XANTHAN GUM | 1.0 |
| CARRAGEENAN | 1.0 |
| SPICES - INCLUDING SALT, LIQUID SMOKE, FLAVOR, PEPPER, GARLIC AND ONION | 1.0 |
| TOTAL | 100.0 |

A process similar to that set forth in Example 42 was undertaken to provide a hamburger flavorant-containing matrix. Initially, the vegetable oil was warmed to a liquid. The spices and xanthan gum were added to the oil and a uniform mixture was obtained. Finally, the maltodextrin was added and uniformly combined with the above ingredients. The resultant mixture was processed at a low setting and a white flake having a strong beef flavor was obtained.

EXAMPLE 44
SAUSAGE FLAVORANT MATRIX

| INGREDIENTS | WEIGHT (%) |
|---|---|
| SACCHARIDE-MALTODEXTRIN D.E. 36 | 78.0 |
| CANOLA OIL | 20.0 |
| SPICES - INCLUDING PORK FLAVOR, FENNEL, SALT, PEPPER AND GARLIC | 2.0 |
| TOTAL | 100.0 |

The procedure set forth in Example is repeated except a flavorant-containing matrix is prepared for sausage meta products instead of hamburger. The ingredients are combined and spun in the manner set forth in Example 42. The spices are uniformly combined with the oil before the saccharide is admixed. The resultant mixture is processed, and a white, pork-flavored flake is obtained.

EXAMPLE 45
HAMBURGER PRODUCT

| INGREDIENTS | WEIGHT (%) |
|---|---|
| GROUND BEEF - 93% LEAN | 95.0 |
| FLAVORANT MATRIX OBTAINED AS A RESULT OF EXAMPLE 42 | 5.0 |
| TOTAL | 100.0 |

EXAMPLE 46
HAMBURGER PRODUCT

| INGREDIENTS | WEIGHT (%) |
|---|---|
| GROUND BEEF - 93% LEAN | 97.0 |
| FLAVORANT MATRIX OBTAINED AS A RESULT OF EXAMPLE 43 | 3.0 |
| TOTAL | 100.0 |

Hamburger-containing meat products were prepared for these examples. In Example 45 the flake matrix obtained as a result of Example 42 was combined with the lean ground beef until a uniform mixture was obtained. In Example 46, the matrix obtained in Example 43 was used. In each example the mixtures were divided and formed into hamburgers. During cooking, the matrix flakes dissolved, releasing the spices and unsaturated oil. The matrix thus provides the texture, moisture level and flavor characteristics of a much higher fat content. With Example 46, it was also observed that the hamburger product prepared with the Example 43 matrix displayed somewhat more cohesiveness and retained juiciness.

Separately, a portion of the ground beef flavorant flake mixture in Example 45 was cooked using a microwave. It was unexpectedly found that the anti-oxidant properties of the saccharide portion of the flake enhanced the stability of the meat so that after microwaving the resultant patty remained moist and was browned during the cooking process. The hamburger was juicy and had a pleasing taste.

EXAMPLE 47
SAUSAGE PRODUCT

| INGREDIENTS | WEIGHT (%) |
|---|---|
| PORK | 92.0 |
| FLAVORANT MATRIX OBTAINED AS A RESULT OF EXAMPLE 44 | 8.0 |
| TOTAL | 100.0 |

The flavor-enhanced sausage product of Example 47 is prepared by combining the pork-flavored matrix with ground pork. The mixture may then be used as sausage patties or to fill sausage casings.

TABLE 1
EXAMPLE 48
SALISBURY STEAK PRODUCT FLAVORANT MATRIX

| INGREDIENTS | WEIGHT (GRAMS) |
|---|---|
| HYDROGENATED MEAT-FLAVORED SOYBEAN OIL (BUNGE CO.) | 100.0 |
| MALTODEXTRINS D.E. 36 | 300.0 |
| CARRAGEENAN | 20.0 |
| ONION POWDER | 50.0 |
| BLACK PEPPER POWDER | 20.0 |
| CELERY SEED POWDER | 10.0 |
| GARLIC POWDER | 1.0 |

A flavorant matrix suitable for Salisbury steak products was prepared for this example. The hydrogenated soybean oil was heated to a liquid. The remaining ingredients were combined separately and thoroughly mixed. The spice-containing mixture was then slowly added to the oil while mixing. The ingredients were then processed at a low temperature to yield flakes having a savory taste and smell.

EXAMPLE 49
SALISBURY STEAK PRODUCT

| INGREDIENTS | WEIGHT (%) |
|---|---|
| FLAVORANT MATRIX AS PREPARED ABOVE | 5.0 |
| GROUND BEEF - 80% LEAN | 95.0 |
| TOTAL | 100.0 |

The flavorant matrix and ground beef were uniformly combined in the ratio set forth above and formed into a steak shape. The steak was cooked for 4 minutes on each side at a temperature of medium-high. The cooked Salisbury steak product was found to have a pleasant taste and aroma.

EXAMPLE 50
SOY BURGER PRODUCT

| INGREDIENTS | WEIGHT (%) |
|---|---|
| SOYBURGER MIX (ADM) | 92.0 |
| FLAVORANT MATRIX OBTAINED AS A RESULT OF EXAMPLE 7 | 8.0 |
| TOTAL | 100.0 |

The flavorant matrix prepared in Example 48 was combined with a soyburger mix obtained from the ADM (Archer Daniels Midland) Company. The flavorant matrix and soyburger mix were uniformly combined and separated into individual patties. The cooked soyburgers were found to have an excellent taste and juiciness.

Other meats and protein media not included in a specific example set forth herein are also contemplated for use in the present invention. For example, horse meat could be used as well as mutton, lamb, venison, and many others.

Examples 51 and 52

Maltooligosaccharides (MOS) have been found especially useful as spun matrix carriers. A maltooligosaccharide is generally a saccharide wherein the polymeric linkage is through the alpha bonds rather than the beta bonds and generally contains less than ten units. The MOS available from Pfanstiehl Laboratories, Inc., No. 138, has a D.E. of 27 and a mono, di-, and tri-saccharide content of 19.4% by weight. It produces large flakes which are suitable as carriers in accordance with the following examples:

Example 51

In this example a high-calorie product useful as an energy source is made with the MOS spun matrix. A mixture was prepared with 75.0 grams (75%) of MOS D.E. 27, 15 grams (15%) corn oil, and 10 grams (10%) smooth peanut butter. The combination was mixed by hand without heating.

The mixture was subjected to flash flow conditions at a low temperature about 140° C. and at a speed of about 3600 r.p.m. The product was a high-energy flake which had an attractive appearance, quite suitable for incorporation in food.

Example 52

Similarly, a mixture was prepared with 57.05 grams (74.0%) of MOS D.E. 27, 5.57 grams (11.1%) salt, and 7.48 grams (14.9%) corn oil and hand-mixed without heat. The mixture had the appearance of a white powder. The powder was subjected to flash flow at about 140° C. and at a speed of about 3600 r.p.m.

The resulting product was in the form of chips having a variety of sizes. The chips were both white and brown, but had a texture and appearance satisfactory for ingestion.

Example 53

In order to determine the ability to delivery high-energy flavor, a test was conducted by hand mixing a combination of 42.5 grams (85%) MOS D.E. 27, 2.5 grams (5%) corn oil, and 5 grams (10%) beef flavor.

While unblended pockets appeared during mixing, when the mixture was subject to flash flow conditions a translucent, light brown flake matrix appeared which had a sweet, beefy flavor.

Example 54

A medicament formulation was tested by blending a combination of 28.6 grams (57.7%) of MOS D.E. 27, 7.1 grams (14.2%) of acetaminophen, and 14.3 grams (28.6%) of vegetable oil.

The blend was subjected to flash flow conditions, converting a powder to high quality white chip which is readily useable in, or as a pharmaceutical delivery system.

Example 55

Another test was conducted to determine whether or not a dye-bearing matrix could be provided. A 50 mg sample of Rhodamine B dye was dissolved in ethanol (1 ml solution of 95% ethanol). 50 grams of MOS D.E. 27 was added and blended by hand.

The blend was subjected to flash flow conditions by spinning at low temperature of about 140° C. at a speed of about 3600 r.p.m. A matrix was recovered in which the dye was substantially evenly dispersed throughout. The yield was about 75%.

Example 56

A second test was conducted similar to that of Example 55, but a greater yield of about 82% resulted.

The product from each of Examples 55 and 56 was readily useable in many applications which dye dispersions are desirable.

Examples 57, 58 and 59

Further tests were conducted as Examples 57, 58 and 59 using the same protocol as in Examples 2, 6, and 16 respectively. The maltodextrin component was replaced with the MOS as described in Examples 51, et seq.

The results were quite favorable. In Example 57, a flake product containing garlic oil was produced which had a strong garlic flavor and which formed a colloid when placed in water. In Example 58, acetaminophen-bearing white particulate was produced which could be easily used as a pharmaceutical delivery means. Similarly, Example 59 resulted in a high quality white particulate which included sucralfate as an active ingredient.

Example 60

A mixture was prepared to contain 67.5% maltodextrins D.E. 36, 25% flour and 7.5% sorbitol. The mixture was then spun at approximately 3600 r.p.m. at 125° C. The resulting maltodextrin matrix was a white, narrow flake. When added to cold water the flour flakes melted into dissolution after only one minute of stirring. Moreover, the resulting solution nicely thickened to uniform viscosity found upon heating. The flakes are therefore well suited for use in food products, such as soups and sauces, where flour is conventionally used as a thickener.

Example 61

A mixture was prepared to contain 50% maltodextrins D.E. 42 and 50% cornstarch. The mixture was then spun in a flash heat process at 150° C. to produce thick, white flakes. The flakes dissolved easily in water, and when heated in a microwave, thickened without clumping. The flakes are therefore well suited for use in food products, such as soups and sauces, where cornstarch is conventionally used as a thickener.

Example 62

A soup was prepared in accordance with the present invention with a corn starch thickener. A mixture was prepared using 38.4% of sifted Knorr brand beef soup (172.8 grams), 10% corn oil (45 grams), 10% of a modified corn starch (45 grams of cold-water-dispersing modified starch sold under the brand name Ultra-Sparse M by the National Starch Company), and 41.6% of powdered glucose solids having a D.E. of 42 (187.2 grams of powdered glucose solids sold by CPC International).

The Knorr beef soup has been presifted through a 250 run mesh. The additional ingredients are then mixed with the Knorr brand beef soup and blended to form a feedstock.

The feedstock was then fed to a spinning head maintained at a temperature of about 52° C. The material was spun at approximately 3600 r.p.m. The process resulted in a very fine, small, slender, light brown flake matrix. The product had a full beef aroma.

The resulting product was comparison tested against the feedstock mixture by introducing to tap water and mixing. The unspun beef stock displayed graininess whereas the spun matrix dissolve readily, dispersed and thickened to a rich beefier taste having a smooth texture. The soup made with the matrix was clearly superior to the unspun product.

Example 63

A mixture was prepared to contain 67.5% maltodextrins D.E. 36, 25% Knox® gelatine, and 6.7% sorbitol. The mixture was then spun at 3600 r.p.m. at a temperature of about 125° C. to produce a white flake matrix. The flakes dissolved easily in hot water and, when refrigerated for approximately one hour, formed a firm gelatine product. The flakes are therefore well suited for use in food products, such as soups and sauces, where gelatine is conventionally used as a thickener.

Example 64

Another matrix was prepared which included a nut paste prepared form peanut butter and corn syrup solids at a ration of 50% peanut butter to 50% corn syrup solids. The 50-50 combination was used as a feedstock in a high speed flash heat processing machine run at 3000 r.p.m. at a temperature of from about 114° to about 118° C. The resulting matrix was in the form of a uniform flake having good color and size consistency as well as flowability.

To a 100 gram sample of the flake, water was added so that the resulting composition included 18% water and 72% matrix by weight. The combination was stirred by hand and permitted to sit. The resulting product was a smooth, uniformly-textured nut cream which was high in flavor and easily spread over a substrate, such as bread or toast.

Example 65

Another example was run similar to Example 67 except that the nut paste-bearing matrix was combined with 2% milk and allowed to stand overnight under refrigerated conditions to test the stability of the viscosity of the product. The results were quite astonishing. The viscosity and flowability of the nut cream after standing overnight under refrigerated conditions were the same as the viscosity achieved immediately after stirring the matrix and the low fat milk. Thus, the stability of the viscosity was excellent. It is believed that low fat milk such as 2% milk, skim milk, or other low fat milk products could be used with great success in providing a reconstituted nut cream product in accordance with the present invention. It is also contemplated that other ingredients such as chocolate syrup or liquid can be used to reconstitute the flake, or in the alternative, can be used in minor amounts to form the actual matrix before being reconstituted.

Example 66

A hazelnut example was prepared by processing hazelnut paste and glucose solids. In particular, a combination of 50% hazelnut paste and 50% by weight glucose solids, 42 D.E. powdered, was blended until a substantially even mixture was achieved. The mixture was introduced to a spinning apparatus in accordance with the present invention operated at about 1800 r.p.m. and at a temperature of from about 95° C. to about 105° C. The speed was increased to around 2100 r.p.m. and the feedstock processed evenly without sticking. The resulting matrix was a tan brown flake having a slender appearance. The flake had a high intensity taste.

In the present example, 47 grams of the flake were added to 10 grams of water and reconstituted to form a very enticing thick dark-brown paste.

The machine used for processing the hazelnut paste as set forth above included a 7 inch cable heater head rather than the ribbon heating head.

Example 67

Another further embodiment includes the use of a nut butter resulting from the process set forth in U.S. Pat. No. 5,079,027 to Wong, et al. The reduced-fat nut butter described therein and all manifestations of the product set forth in the '027 disclosure can, in turn, be combined with maltodextrin at appropriate ration and spun to form the nut matrix of the present invention. The matrix can then be reconstituted by use of a liquid such as water, low fat milk, etc., to provide a high flavor low-fat calorie nut cream.

Example 68

A mixture of 35 percent κ carrageenan and 65 percent maltodextrin, D.E. 42, was spun in a flash heat process machine at r.p.m. at a temperature of about 135° C. The procedure produced a uniform white flake. Two (2) grams of the flake product was added to 100 ml of water and subjected to only slight stirring to produce a clear solution. The solution was then heated to about 61° C. and permitted to cool to a solid gel. The gel was clear and showed no separation of water. Thus, the gel product prepared in accordance with the invention provides an excellent meat bulking medium which is clear and which ties up or binds water within the gelled medium.

Example 70

A mixture of 30 percent κ carrageenan, 30 percent crystalline fructose and 60 percent maltodextrin, D.E. 42, was spun in a flash heat process machine at 3600 r.p.m. at a temperature of about 135° C. The procedure produced a uniform white flake. Two (2) grams of the flake product was added to 100 ml of water. A clear solutions was instantaneously realized, with no stirring or mixing required. The solution was then heated to about 61° C. and permitted to cool to a solid gel. The gel was clear and showed no separation of water. Thus, the gel product prepared in accordance with the invention provides an excellent meat bulking medium which is clear and which ties up or binds water within the gelled medium.

A comparison of the results of Examples 68, 69 and 70 demonstrates the advantages of the present invention. In Example 68, representing a simple admixture of carageenan and maltodextrin, combining the admixture with water required mixing, and the gel which was thus formed was cloudy and demonstrated water separation. On the other hand, in Example 69, representing a flash-flow formed matrix incorporating carrageenan and maltodextrin according to one embodiment of the present invention, the matrix completely dissolved in water with only slight stirring, and produced a clear gel with no separation of water. Further, in Example 70, representing a flash-flow formed matrix incorporating carrageenan, maltodextrin and a sugar according to yet another embodiment of the present invention, the matrix instantaneously and completely dissolved in water with no stirring or mixing required, and produced a clear gel with no separation of water.

Example 71 (Comparative Example)

Two types of xanthan gum ingredients, very finely dispersed xanthan gum and agglomerated xanthan gum, were each mixed separately with maltodextrin having a D.E. of 42. The two mixtures were formulated with 35% xanthan gum and 65% maltodextrin. Two (2) gram samples of each mixture were added to separate vessels each having 100 ml of water and mixed. The mixture which included the very finely dispersed xanthan gum did not go into solution and "fish eyes" were formed by wetting of the surface of clumps of xanthan gum. The mixture which included agglomerated xanthan gum solubilized only slightly resulting in clumps of agglomerated xanthan gum even after sitting over 24 hours. Neither vessel contained a xanthan gum solution which could be used without further treatment such as high speed agitation or stirring and/or the use of a wetting agent, such as propylene glycol esters.

Example 72

Very fine xanthan gum was mixed with maltodextrin having a D.E. of 42. The mixture was processed in accordance with the present invention by feeding into a spinning machine operated at 3600 r.p.m. at a temperature of about 135° C. The feedstock was converted to a white flaky matrix. A two (2) gram sample was added to 100 ml of water and stirred slightly. Inspection showed that the xanthan gum ingredients were completely and uniformly dissolved. The solution was permitted to stand for more than 24 hours, and reinspection reveled substantially no separation. The solution could be readily used in a food composition, such as salad dressing, et al., without further processing. Thus, very-low-oil and low-sugar food systems could be produced using the xanthan gum solutions.

Example 73

Very fine xanthan gum was mixed with maltodextrin having a D.E. of 42 and a sugar. The mixture was processed in accordance with the present invention by feeding into a spinning machine operated at 3600 r.p.m. at a temperature of about 135° C. The feedstock was converted to a white flaky matrix. A two (2) gram sample was added to 100 ml of water. Inspection showed that the xanthan gum ingredients were instantaneously completely and uniformly dissolved, without the need for any mixing or stirring. The solution was permitted to stand for more than 24 hours, and reinspection revealed substantially no separation. The solution could be readily used in a food composition, such as salad dressing, et al., without further processing. Thus, very-low-oil and low-sugar food systems could be produced using the xanthan gum solutions.

A comparison of the results of Examples 71, 72 and 73 demonstrates the advantages of the present invention. In Example 71, representing a simple admixture of very fine xanthan gum and maltodextrin, the admixture did not go into solution with water even with mixing, and "fish-eyes" were formed. On the other hand, in Example 72, representing a flash-flow formed matrix incorporating very fine xanthan gum and maltodextrin according to one embodiment of the present invention, the matrix completely dissolved in water with only slight stirring, and produced a clear gel with no separation of water. Further, in Example 73, representing a flash-flow formed matrix incorporating xanthan gum, maltodextrin and a sugar according to yet another embodiment of the present invention, the matrix instantaneously and completely dissolved in water with no stirring or mixing required, and produced a clear gel with no separation of water.

Interestingly, gums are most beneficial when used in very fine dispersion form. However, very fine gum dispersions are the most difficult to incorporate satisfactorily into foods because of their surface-wetting-interior-clumping characteristic. Actually, it is not possible to incorporate very fine gums in food without the assistance of high speed stirring and/or wetting agents. The present invention has completely overcome this difficulty.

Gums can be included in the matrix of the present invention in a range of from 0.5% up to about 60%, with a preferred range being from about 30% to about 38%. Once again, deionized maltodextrin has been found to be the most beneficial carrier for implementing the present invention.

Example 74

A mixture of 35 percent carrageenan, 54 percent corn syrup solids having a Dextrose Equivalent of 42, 10 percent crystalline fructose dn 1 percent distilled monoglycerides was spun in a flash heat process machine at 3600 r.p.m. at a temperature of about 135° C. A uniform white flake was produced. Two (2) grams of the flake product was added to 100 ml of water at room temperature. The flake product instantaneously and completely dissolved in the water. The solution was permitted to stand for more than 24 hours, and no water separation occurred.

While there have been described what are presently believed to be the preferred embodiments of the invention, those skilled in the art will realize that changes and modifications may be made thereto without departing from the spirit of the invention, and it is intended to claim all such changes and modifications as fall within the true scope of the invention.

What is claimed is:

1. A saccharide-based matrix comprising a maltodextrin feedstock including a gelling agent and a sugar, said feedstock having been subjected to conditions of force and temperature which induce flash flow of said feedstock whereby said matrix possesses physically- or chemically-altered structure from said feedstock.

2. The saccharide-based matrix of claim 1 wherein said maltodextrin is deionized.

3. The saccharide-based matrix of claim 1 wherein said conditions which induce flash flow comprise subjecting said feedstock simultaneously to flash heating and applied physical force.

4. The saccharide-based matrix of claim 3 wherein said conditions are created by subjected said maltodextrin feedstock to a flash flow process.

5. The saccharide-based matrix of claim 3 wherein said applied physical force is centrifugal.

6. The saccharide-based matrix of claim 1 wherein said gelling agent is selected from the group consisting of xanthan gum, gelatin, guar gum, pectin, carrageenan gum, gum tragacanth, alginates, gum kayara, locust bean gum, gum acacia, agar gum, cellulose gum, and mixtures thereof.

7. The saccharide-based matrix of claim 1 wherein said gelling agent is present in an amount of from about 3% to about 50% by weight of said matrix.

8. The saccharide-based matrix of claim 8 wherein said gelling agent is present in an amount of from about 5% to about 20% by weight of said matrix.

9. The saccharide-based matrix of claim 1 wherein said sugar is selected from the group consisting of sucrose, fructose, dextrose, mannitol, sorbitol, flucose, lactose, maltose, and mixtures thereof.

10. The saccharide-based matrix of claim 1 wheren said sugar is present in an amount of from about 5% to about 30% by weight of said matrix.

11. The saccharide-based matrix of claim 10 wherein said sugar is present in an amount o ffrom about 10% to about 20% by weight of said matrix.

12. The saccharide-based matrix of claim 1 which furhter comprises an x-ray contrast agent.

13. The saccharide-based matrix of claim 12 wherein said contrast agent is Barium Sulfate ($BaSO_4$.

14. The saccharide-based matrix of claim 1 wherein said feedstock further comprises a component selected from the group consisting of oleaginoius materials, food ingredients, pharmaceuticals, cosmetics, emulsifiers, and mixtures thereof.

15. A saccharide-based gelling composition instantaneously dispersible in aqueous liquid to be gelled comprising a matrix formed by subjecting a feedstock comprising maltodextrin, a gelling agent and a sugar to conditions of force and temperature which induce flash flow of said feedstock whereby said matrix possesses physically- or chemically-altered structure from said feedstock.

16. A composition for use as a contrast medium comprising a matrix prepared by subjecting a feedstock comprising maltodextrin, gum, sugar, and a contraste agent to conditions which induce flash flow.

17. The composition of claim 16 which further comprises water added in a sufficient amount to provide a contrast medium for ingestion by a patient who is subsequently subjected to x-ray analyses.

18. The composition of claim 17 wherein said contrast agent is varium sulfate ($BaSo_4$).

19. A method of preparing a saccharide-based matrix comprising subjecting a maltodextrin feedstock including a gelling agent and a sugar to conditions of force and temperature which induce flash flow of said feedstock whereby said matrix possesses physically- or chemically-altered structure from said feedstock.

20. The method of claim 19 wherein said maltodextrin is deionized.

21. The method of claim 1 wherein said conditions which induce flash flow comprise subjecting said feedstock simultaneously to flash heating and applied physical force.

22. The method of claim 19 wherein said conditions are created by subjecting said maltodextrin feedstock to a flash shear process.

23. The method of claim 19 wherein said feedstock further comprises a member of the group consisting of oleaginous materials, food ingredient materials, pharmaceutical, cosmetics, emulsifiers, and mixtures thereof.

24. A method of dispersing gelling agents in aqueous medium comprising adding to an aqueous medium a saccharide-based matrix prepared from a feedstock comprising meltodextrin, a gelling agent, and a sugar to conditions which induce flash flow of said maltodextrin whereby said matrix possesses physically- or chemically-altered structure from said feedstock.

\* \* \* \* \*

UNITED STATES PATENT AND TRADEMARK OFFICE
CERTIFICATE OF CORRECTION

PATENT NO. : 6,337,082 B1　　　　　　　　　　　　　　　　　　　　　　　　　　　Page 1 of 1
DATED : January 8, 2002
INVENTOR(S) : Richard C. Fuisz and Robert K. Yang It is certified that error appears in the above-identified patent and that said Letters Patent is hereby corrected as shown below:

<u>Title page,</u>
Insert:
-- [73]   Assignee:  Biovail Technologies Ltd., Virginia (USA) --

Signed and Sealed this

Twenty-first Day of October, 2003

JAMES E. ROGAN
*Director of the United States Patent and Trademark Office*